(12) United States Patent
Lackritz et al.

(10) Patent No.: US 6,956,651 B2
(45) Date of Patent: Oct. 18, 2005

(54) BIOANALYSIS SYSTEMS INCLUDING OPTICAL INTEGRATED CIRCUIT

(75) Inventors: Hilary S. Lackritz, 10952 Barranca Dr., Cupertino, CA (US) 95014; John Kenney, Palo Alto, CA (US); Ian Gibbons, Portola Valley, CA (US); Anthony J. Ticknor, Cupertino, CA (US)

(73) Assignee: Hilary S. Lackritz, Cupertino, CA (US)

( * ) Notice: Subject to any disclaimer, the term of this patent is extended or adjusted under 35 U.S.C. 154(b) by 0 days.

(21) Appl. No.: 10/657,482

(22) Filed: Sep. 8, 2003

(65) Prior Publication Data
US 2004/0046963 A1 Mar. 11, 2004

Related U.S. Application Data
(60) Provisional application No. 60/408,821, filed on Sep. 7, 2002.

(51) Int. Cl.[7] ............................................... G01N 21/55
(52) U.S. Cl. ....................................................... 356/445
(58) Field of Search ......................................... 356/445

(56) References Cited

U.S. PATENT DOCUMENTS

| 4,394,060 A | * | 7/1983 | Verber et al. .................. 385/7 |
| 5,912,181 A | | 6/1999 | Petcavich |
| 5,917,607 A | * | 6/1999 | Naya ........................... 356/445 |
| 5,922,594 A | | 7/1999 | Lofas |
| 5,955,729 A | | 9/1999 | Nelson et al. |
| 5,965,456 A | | 10/1999 | Malmqvist et al. |
| 5,972,612 A | | 10/1999 | Malmqvist et al. |
| 6,008,893 A | | 12/1999 | Roos et al. |
| 6,127,183 A | | 10/2000 | Ivarsson et al. |
| 6,143,513 A | | 11/2000 | Lofas |
| 6,143,574 A | | 11/2000 | Karlsson et al. |
| 6,200,814 B1 | | 3/2001 | Malmqvist et al. |
| 6,207,381 B1 | | 3/2001 | Larsson et al. |
| 6,289,286 B1 | | 9/2001 | Andersson et al. |
| 6,330,062 B1 | | 12/2001 | Corn et al. |
| 6,417,924 B1 | | 7/2002 | Kimura |
| 6,417,925 B1 | | 7/2002 | Naya |
| 6,421,128 B1 | | 7/2002 | Salamon et al. |
| 6,424,418 B2 | | 7/2002 | Kawabata et al. |
| 6,570,657 B1 | * | 5/2003 | Hoppe et al. ................ 356/445 |

OTHER PUBLICATIONS

International Search Report, PCT/US03/27918, Jul. 29, 2004.

R.D. Harris and J.S. Wilkinson, Waveguide Surface Plasmon Resonance Sensors, University of Southampton 1994.

* cited by examiner

Primary Examiner—Richard A. Rosenberger
(74) Attorney, Agent, or Firm—Amin & Turocy, LLP

(57) ABSTRACT

Optical Integrated Circuits (OIC) in Surface Plasmon Resonance (SPR) Analysis Systems combined with micorarray or microwell plates to provide enhanced sensitivity, stability, speed of analysis and reduced size are disclosed. Using the OIC with other optical analysis methods to provide enhance analysis systems is also disclosed.

23 Claims, 8 Drawing Sheets

BIOANALYSIS SYSTEMS INCLUDING OPTICAL INTEGRATED CIRCUIT

RELATED APPLICATIONS

This application claims priority to provisional application Ser. No. 60/408,821 filed Sep. 7, 2002, the contents of which are incorporated herein.

FIELD OF THE INVENTION

The present invention generally relates to bioanalysis systems and methods, such as Surface Plasmon Resonance systems, involving optical circuits. In particular, the present invention relates to using optical circuits to improve management of light in bioanalysis systems such as Surface Plasmon Resonance and providing improved sample arrays.

BACKGROUND OF THE INVENTION

The pharmaceutical industry is involved in the discovery and development of medicines that improve our health. Drug discovery and development requires vast sums of money and inordinate amounts of time. Specifically, current methods used to identify and validate "targets" and to optimize drug structures in the pharmaceutical industry are particularly difficult and inefficient in large measure due to deficiencies in analytical techniques. An appropriately chosen detection technology and the instrumentation required to perform the detection are vital to the success of any assay. This is particularly true for high throughput screening, which requires continually higher throughput, lower costs, and higher sensitivities for lower quantities of reagents.

A variety of analytical techniques are used to characterize interactions between molecules, particularly in the context of assays directed to the detection and interaction between biomolecules and of biomolecules with small chemical entities. For example, antibody antigen interactions are of fundamental importance in many fields, including biology, immunology and pharmacology. In this connection, many analytical techniques involve binding of a "receptor" such as an antibody to a support, and contacting the bound receptor with an "analyte" such as an antigen. After contact between the receptor and analyte, one or more characteristics are measured which are indicative of the interaction, such as the ability of the receptor to bind the analyte.

There are numerous methods of studying protein protein interactions, including fluorescence, surface plasma resonance, mass spectrometry, and chemiluminescence. The goal of these studies is to determine what the protein of interest interacts with and how specific are the interactions. The data from these assays provides information on how proteins function in biological systems.

In the important and economically significant field of Medical Diagnostics, a variety of assay types are performed for many analytes of many different (chemical) types. The analytes are typically substances that indicate the health or disease status of a human or animal subject. Also, analytes that indicate the status of therapy are of great interest. There is a broad, unmet need in this field for general methods to measure accurately and reliably ligand-receptor interactions. Presently, most methods currently used in the diagnostics industry use employ labels such as a fluor. There is an increasing need however for measurements of many analytes in a single specimen. Moreover, the activities of the Human Genome Project and the burgeoning field of proteomics are identifying many new analytes and there is a pressing need for methods by which valid new assays can be developed quickly.

Surface Plasmon Resonance (SPR) is a "label free" method of assay development and is promising due to the possibility that it is faster to develop for any specific application and more reliable than label requiring methods such as those based on fluorescence. SPR systems and methods are known. Generally speaking, SPR is observed as a change such as a dip or reduction in intensity of light reflected at a specific angle from the interface between an optically transparent material and a thin metal film, and depends on among other factors the optical path length, i.e., the integral product of refractive index and physical thickness, of the medium and the quantity and distribution of such refractive material close to the metal surface. A change of refractive properties at the metal surface, such as by the adsorption or binding of material with different optical properties (typically index of refraction) than the medium in which the SPR metal surface is immersed, causes a corresponding shift in the angle at which maximum SPR occurs and which can be related quantitatively to the quantity of material that binds or adsorbs. To couple the light to the interface with the assay such that SPR arises, alternative arrangements are used; either a metallized diffraction grating (Wood's effect), or a metallized glass prism or a prism in optical contact with a metallized glass substrate (Kretschmann effect).

While SPR is a promising technology, there are concerns associated with SPR that inhibit its wide spread use. One problem is that conventional methods for SPR lead to less sensitive results than fluorescence results. Another problem is that SPR has not been capable of high-throughput in terms of assays/unit time. Yet another limiting factor is non-specific binding to the sensing surface, a problem common to all types of direct-measuring sensors, i.e. where no labelled reagent, such as an enzyme or a fluorophore, is used to provide the detected signal. Since SPR generates a signal for all material bound to the surface having an index of refraction different than the surrounding ambient medium (solution), the analyte cannot be distinguished from non-specific material.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

The present invention provides systems and methods that mitigate problems associated with the inefficient management of light in conventional SPR systems. In this connection, the inventors have discovered that many of the concerns associated with SPR are attributable to the inefficient management of light. Optical Integrated Circuits (OICs) are integrated into SPR systems to provide advances such as high throughput and high sensitivity which consequently make SPR a much more attractive technology in drug discovery. The bioanalysis systems and methods of the present invention permit faster and simpler discovery of new targets for drugs, identification of such targets, and screening candidate entities as directed to the targets. Moreover, the present invention enables the identification of receptors for targets of unknown function.

One aspect of the invention relates to a bioanalysis system, such as an SPR system, containing a light source; a metallic support; a light detector, such as reflectance spectrophotometer; and at least one OIC. Another aspect of the invention relates to a method of monitoring a binding event, involving directing light at a metallic support, detecting light reflected from the metallic support, and analyzing properties of the reflected light, wherein directing light and/or detecting light involves the use of an OIC, or the light detector may be part of the OIC.

Another aspect of the invention relates to a disposable microwell array for the bioanalysis system, such as the SPR system, containing a silicon substrate having an insulation layer formed thereover; a plurality of wells formed on a top surface of the silicon substrate; and a metallic layer on the silicon substrate within each of the wells. A first member of a binding pair may be attached to the metallic layer in some cases with appropriate intermediate linking layers while a second member of a binding pair is contacted with the first member simply by exposure to a sample solution and a second reagent. A glass or plastic substrate may be employed in place of the silicon substrate.

Another aspect of the invention relates to a method analyzing distribution in a Z direction and orientation of mass relative to a planar or graded (continuous or not continuous) SPR surface using at least one of multiple wavelengths, physical surface modification, depth profiling, and polarization analysis. The Z direction is normal to the SPR surface. The method permits the evaluation of specific binding versus nonspecific absorption and concentration and binding profiles of specifically bound mass.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION OF THE INVENTION

Figure 1:
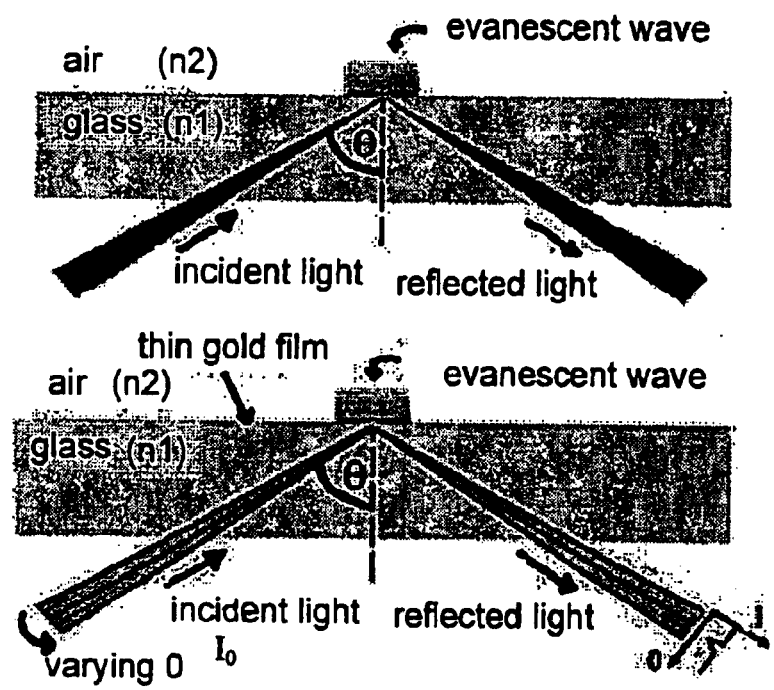
FIG. 1 shows some of the basic principles of SPR.

There are three aspects to studying protein-protein interactions surface chemistry, protein purification and capture agents, and detection technologies required to study these interactions. The present invention is particularly useful for the detection of protein-protein interactions.

OICs, such as PLCs, are employed in bioanalysis systems and methods to facilitate monitoring binding interactions between Members of a Binding Pair (MBPs). That is, binding events between MBPs can be efficiently measured using an SPR system containing at least one OIC. Generally speaking, SPR relates to an electron charge density wave phenomenon that arises at a surface of a metallic film when light is reflected at the film under certain conditions. In this context, analysis is accomplished by measuring a change in the SPR due to effects caused by binding of MBPs on/near the metal surface. The efficient measurement and handling of light by the OICs permit high throughput in SPR.

The present invention involves the use of detection technologies that utilize optical biosensors that exploit surface plasmon resonance, waveguides and resonant mirrors. These sensors allow the study of affinity and real time kinetic of a wide variety of molecular interactions, without the use of any molecular tag or label traditionally used in many bioassay including protein:protein interactions. Advances in instrumentation provided by the present invention enable increasing use of optical biosensors in basic science research, drug discovery and diagnostics. Particular interest in the area of drug discovery where increasing use of biosensor technology is seen in applications like target identification, "ligand fishing", and confirmation of high throughput "hits" using optical biosensors as an information-rich secondary screen. Additionally, real time characterization of interactions and affinities of confirmed hits, integration of mass spectrometry in proteomics, determination of drug binding to serum proteins, and adsorption of drug to membrane interfaces are enabled. Process control and production for good laboratory practice (GLP)/and Good manufacturing process (GMP) validation, analysis of clinical samples, screening of membrane receptors, development of multiplex assay for high-information content, high throughput screening are also applications that are facilitated by the present invention.

The detection technology of the present invention offers high sensitivity and high throughput without the use of label and is a significant improvement in performance to existing biosensor technologies. Higher sensitivity, along with disposable consumables uniquely brings the technology in par with fluorescent assays, which are widely used methods of detection. The labeling step required by all fluorescence-based methods imposes burdensome time and cost requirements and in some cases may interfere with molecular interactions by occluding a binding site, which leads to false negatives. In this connection fluorescent compounds are typically hydrophobic, creating background problems leading to the false positives.

Generally speaking, OICs permit manipulation of light as they allow branching, coupling, switching, separating, high resolution spectral analysis, multiplexing and demultiplexing of optical signals without intermediate transformation between optical and electrical media. An OIC uses waveguides to guide light and perform various functions. OICs that may be employed in SPR systems include one or more of PLCs, arrayed waveguide gratings (AWGs), multiplexers such as wavelength division multiplexers (WDMs) and optical add/drop multiplexers (OADMs), demultiplexers, optical switches, multichannel waveguide lasers, variable optical attenuators (VOAs), splitters, couplers, taps, filters, and the like. Optical switches include 1×2 switches/splitters, 2×2 switches/splitters, 1×N switches/splitters, 2×N switches/splitters, N×M switches/splitters, and the like. OICs provide improvements to SPR and permit the efficient use of optical fibers within an SPR system.

In addition to SPR methods, the systems and methods of measuring a change of the refractive index as being indicative of the binding MBP include both internal and external reflection methods. For example, such additional methods include ellipsometry, external Brewster angle reflectometry, and evanescent wave reflectometry, the latter including Brewster angle reflectometry, critical angle reflectometry, SPR reflectometry, evanescent wave ellipsometry, scattered total internal reflection (STIR), optical waveguide sensors, refractometric optical fiber sensors, fluorescence, evanescent wave based imaging, such as critical angle resolved imaging, Brewster angle resolved imaging, SPR angle resolved imaging; and the like. These methods and the components required to perform them are collectively referred to as bioanalysis systems. In this connection, the present invention generally relates to OIC bioanalysis systems. Although the present invention is discussed in detail for SPR, the same concepts, devices, and methods may be applied to any of the additional OIC bioanalysis systems.

The practical consequence of this interaction is that the concentrations of specific molecules can be quantitatively measured by observing the SPR shifts that occur when the molecules bind to the surface of a support sensor. In a support sensor, a gold (or other metal) surface is coated with a MBP which may be antibodies, DNA probes, enzymes or other reagents chosen because they interact exclusively with a selected target, analyte or molecule. When the support sensor is exposed to a sample that contains analyte molecules, they bind to the sensor's surface via their specific interaction with the surface attached MBP. Over a range of solution concentration that typically begins at zero and extends to within approximately at least 50% of the concentration at which all the surface attached MIPs are occupied by molecules from solution, the amount of binding that occurs is proportional to the concentration of the analyte in the sample solution. This binding event changes the composition of the medium at the surface and produces a SPR shift. The magnitude of the shift is typically proportional to the amount of binding that takes place, in particular when there are no strong interactions between adjacent bound molecules and when the extent of binding is less than approximately 50% of the saturation occupancy of the binding layer. Comparison of the observed SPR shift with a stored calibration curve yields a quantitative measurement of the concentration of the analyte in the sample.

When PLCs are employed as one of the light handling components in an SPR system, the SPR signal associated with binding events can be deconvoluted, thereby improving accuracy, sensitivity, and reliability of information generated therefrom. For example, in instances where multiple sources of light are employed, a multiplexer effectively combines various paths and/or wavelengths into a single light path, such as an optical fiber. A PLC switch can direct light to the metallic surface where binding events occur without mechanical movement. In fact, OICs can effectively change, control, and/or measure the location, intensity, and dispersion of light, in a static or dynamic fashion.

OICs such as optical switches permit the delivery of light to specific locations on the SPR metallic support (such as to different wells on the SPR metallic support), and can permit the delivery of light to specific, different locations within a well on the SPR metallic support. This feature contributes to the ability to distinguish between non specific binding and specific binding, since specific binding can be caused to occur at discrete locations while non specific binding occurs at all locations (generally). Thus, a defined region or zone of the metallic support within one well can be used as an internal reference, the signal for example being subtracted from that generated by the detecting region or zone of the same metallic support to correct for nonspecific adsorption or binding. Moreover, OICs and optical fibers permit delivery of light to the SPR metallic support and collection of reflected light from the SPR metallic support. OICs permit control over the precise angles and wavelengths employed for incident light. OICs enable optimum combinations of angle(s) and wavelength(s) in SPR methods and higher sensitivity at a given wavelength.

Generally speaking, SPR relates to an electron charge density wave phenomenon that arises at a surface of a metallic film when light is reflected at the film under certain conditions. In this context, analysis is accomplished by measuring a change in the SPR due to effects caused by binding of MBPs on/near the metal surface. The efficient measurement and handling of light by the OICs permit high throughput in SPR.

SPR is a quantum optical-electrical phenomenon arising from the interaction of light with a metal surface. Under certain conditions the energy carried by photons of light is transferred to packets of electrons, called plasmons, on a metal's surface. Energy transfer occurs only at a specific resonance wavelength of light at a specific angle of interaction of the light and the plane of the metal surface. That is, the wavelength where the quantum energy carried by the photons exactly equals the quantum energy level of the plasmons. The plasmon state is highly delocalized and formed collectively through Coulombic (electrostatic) interaction of weakly bound electrons. Both metals and nonmetals, including plastics, show plasma energy losses. The lost energy may reappear in the form of ultraviolet or visible radiation; no chemical effect is known to have occurred from such losses.

SPR stems from one of the principles of optics: those of total internal reflectance, or TIR. This is illustrated in FIG. 1, as occurring at the interface between materials with differing refractive indices n1 and n2. Total reflection occurs above a critical angle, when $n1>n2$. At the same time, an evanescent electromagnetic wave propagates away from the interface. SPR occurs when a thin electrically conducting film is placed at the interface between the two optical media. At a specific incident angle, greater than the TIR angle, the surface plasmons (oscillating electrons at the edges of the metal) in the conducting film resonantly couple with the light because their frequencies match. Since energy is transferred from the photons to the plasmons in this resonance, the reflected intensity, I, shows a drop at the angle and wavelength where SPR is occurring, as shown.

The resonance wavelength can be determined very precisely by measuring the light reflected by a metal surface at a particular angle. At most wavelengths the metal acts as a mirror, reflecting virtually all the incident light. At the wavelength that fulfills the resonance conditions for the selected angle, the incident light is almost completely absorbed by the generation of the plasmons. The wavelength at which maximum light absorption occurs is the resonance wavelength. The measuring device for SPR is a simple, but highly sensitive, reflectance spectrophotometer.

The coupling of light into a metal surface results in the creation of a plasmon, a group of excited electrons that behave like a single electrical entity. The plasmon, in turn, generates an electrical field that extends about 100 nm above and below the metal surface. The characteristic of this phenomenon that makes SPR an analytical tool is that any change in the chemical composition of the environment within the range of the plasmon field that causes a change in the optical properties of that environment (most typically the integral product of the index of refraction and physical thickness of a layer or film within that environment) will change the wavelength of light that resonates with the plasmon. That is, a chemical change results in a shift in the wavelength of light that is absorbed rather than reflected and the magnitude of the shift is quantitatively related to the magnitude of the optical change which, in many cases, is proportional to the chemical change of a determined range of parameters. In many situations, the magnitude of the signal change can be related to the amount of mass adsorbed or desorbed on or from the surface of the SPR device.

The use of OICs containing slab optical waveguides in SPR sensors provides numerous attractive features such as a simple way to control and guide the optical path in the sensor system (efficient control of properties of the light, suppression of the effect of stray light, etc.), small size, reproducibility, and ruggedness. A lightwave is guided by the waveguide which is in close physical proximity to a single use disposable used to perform assays and enters a region with a thin metal layer and, entering the region with a thin metal overlayer, it evanescently penetrates through the metal layer. If the surface plasma wave (SPW) and the guided mode are phase-matched, the light wave excites an SPW at the outer interface of the metal.

Plasmons, although composed of many electrons, behave as if they were single charged particles. Part of their energy is expressed as oscillation in the plane of the metal surface. Their movement, like the movement of any electrically charged particles, generates an electrical field. The plasmon's electrical field extends about 100 nm perpendicularly above and below the metal support surface in the situation that the index of refraction of the material(s) above and below the metal surface is small and real (i.e., for dielectric materials such as air, vacuum, glass and other solid state electrical insulators, water, organic chemicals including polymers and plastics, as well as biological molecules and polymers). The interaction between the plasmon's electrical field and the matter within the field determines the resonance wavelength. Any change in the composition of the matter that affects the optical properties within the range of the plasmon's field causes a change in the wavelength of light that resonates with the plasmon. The magnitude of the change in the resonance wavelength, the SPR shift, is directly and linearly proportional to the change in composition of the material in the illuminated zone such that a change in composition causes a directly proportionate change in the integral optical thickness of material(s) within said range of the plasmon's field.

SPR coupling occurs when the incoming light mode matches to the resonance mode of the metal. Since the wave vector of the SPR wave at a metal dielectric interface is greater than the wave vector of the incident light parallel to the interface a high index prism is used. The SPR wave is excited by the evanescent wave present in total internal reflection from the glass to the metal. The mode matching occurs at a specific angle and wavelength for the metal and dielectric indices that are adjacent to the metal. The SPR condition occurs when the metal has a lower real part of the index than the glass, metals such as gold, silver, and molybdenum are typically used. The glass typically has an index in the range from about 1.3 to about 2.2, such as from about 1.44 to about 2.1, in the wavelength range from about 390 nm to about 2500 nm, such as the range from about 400 nm to about 2000 nm. The SPR analysis systems of the present invention are directed to biological systems so the analyte is typically aqueous with an index from about 1.1 to about 1.5, such as about 1.33. The bound material typically has an index from about 1.3 to about 1.7, such as from about 1.4 to about 1.55 depending on the specific structure. The difference in the index at the metal surface between the nonbound and bound condition gives a difference in SPR resonance conditions and thus the angle or wavelength for mode matching.

In one embodiment, the SPR spectrum is obtained by reflection. In another embodiment, the SPR spectra is obtained by transmission. For example, the SPR spectra can be obtained in transmission through nanometer size island structures of metal, such as gold or silver. The transmission angle of maximum intensity provides the SPR angle and is sensitive to the index of the analyate in the same way as reflection SPR. The reflected SPR light has a phase change associated with the index of the analyte. The phase change can be used to produce an image of the surface.

In one embodiment, SPR is carried out in a prism coupled configuration. In another embodiment, SPR is carried out in a waveguide configuration. The light propagates along the waveguide and at the correct/desired wavelength and mode angle the light couples to the surface plasmon mode. This leads to a large increase in attenuation in the waveguide. The wavelength for the plasmon mode depends on the indexes of the covering media, just as in a prism coupled configuration.

The present invention provides greatly improved SPR performance characteristics at a cost significantly lower than existing methods. For example, measurement of low molecular weight analytes is enabled, assays for macromolecules with 100 fold higher sensitivity is facilitated; and assay arrays (especially for proteomic applications) with greatly increased numbers of elements can be constructed.

High assay sensitivity in particular is facilitated by the present invention. Assay sensitivity of the present invention is greatly improved by one or more of three factors: the ability to successfully employ relatively long wavelengths; measurement in the "wavelength domain"; and greater stability of the optics of the OICs compared with free space optics. These factors effectively address two applications which are currently problematic for conventional SPR systems. First, measurement of binding of small molecules is difficult using conventional SPR systems. Since SPR responds to changes of bound mass, it becomes less sensitive on a molar basis when binding of small molecules is being measured. In particular, accurate measurement of compounds in the size range of greatest interest for drug candidates, for example from about 200 to about 2000 Daltons, is difficult. Second, when attempting to measure the binding of macromolecules (MW>2000) with high sensitivity, it is often desirable to measure protein concentrations in the pM range. However, conventional SPR systems measure in the nM range. The present invention facilitates the measurement of the binding of small molecules as well as the measurement of the binding of macromolecules.

One factor in the sensitivity of nonlabeled assay systems such as SPR is the ability to discriminate "specifically" bound matter from that bound non-specifically. Conventional SPR methods rely solely on the specificity of the assay chemistry. The present invention enables optical discrimination of specific from non-specific binding by analysis of the distribution of matter as a function of distance and angular orientation from the receptor surface using one or more of light of different wavelengths, polarized light and analysis of birefringence of the reflected light. The ability to discriminate between specific and non-specific binding is an advantage associated with the present invention.

Conventional SPR systems measure changes in reflectance at a fixed wavelength as a function of the angle between the reflected light and some reference vector such as the input light beam. However, there is not a desirable response of such a system to changes of refractance (and hence analyte concentration) at the illuminated surface. The range of concentrations measurable (dynamic range of the assay) is limited by the lowest concentration measurable and the highest concentration measurable. This range is limited in conventional SPR methods by low sensitivity and/or the loss of resolution that occurs when reflectance is reduced to almost zero as it is at high concentrations of bound analyte. The present invention enables a wider dynamic range by at least one of lowering the lowest concentration measurable and allowing measurements at a variety of wavelengths, some of which are optimal and others not optimal for high sensitivity. At the sub-optimal wavelengths, reflectance is not reduced to zero even at high concentrations of bound analyte thereby permitting accurate measurement of bound analyte.

Conventional SPR systems are limited in throughput because of the limitations of free space optics. OIC based optics such as PLC based optics enable a high number of closely spaced (separated by submillimeter distance) assay locations to be interrogated rapidly (each measurement requiring only a few milliseconds) in a serial or raster fashion without the need to increase the bulk and complexity of instrumentation. In this way, many assays can be monitored essentially simultaneously supporting a throughput of hundreds of assays per minute. In one embodiment, the SPR systems of the present invention can monitor binding of MBPs in/on at least about 100 assay locations on a single substrate. In another embodiment, the SPR systems of the present invention can monitor binding of MBPs in/on at least about 225 assay locations on a single substrate. In yet another embodiment, the SPR systems of the present invention can monitor binding of MBPs in/on at least about 400 assay locations on a single substrate.

An OIC, such as a PLC based integrated optical element, that combines very precise wavelength resolution and capability for optical switching in both time and space is inherently much more stable than any alternative optical scheme, especially those schemes using free space optics. Greater optical stability translates into greater assay precision and sensitivity. PLC optical elements can be easily replicated with very high reproducibility providing for ease of manufacture of many identical instruments. In other words, PLC based optics can be fabricated less expensively than free space optical systems. PLC optical elements are typically much smaller and require much less physical space within an instrument than do free space optics.

OICs guide light by means of planar waveguides between the various integrated elements, such as splitters, switches and Arrayed Waveguide Gratings (AWG) that are used as wavelength dispersive elements. The OICs are compact in size compared to discrete optical elements, even compared to micro optic elements. Because the light is confined in the waveguide between the elements there are none of the problems with stability when free space optics are used. For example, an AWG can provide a high resolution between adjacent optical channels in an OIC having a size less than 5 cm by 8 cm when made in silica based OIC. If an indium phosphide based OIC is employed, the size becomes less than 1 cm on each side. Even the larger size AWG is smaller than the light handling elements in a conventional optical spectrometer with comparable resolution. There are many configurations that are possible in designing a SPR instrument in accordance with the present invention.

In one configuration the OIC allows the light source(s), detectors, optical sample site switches and sampling site to be integrated onto a single circuit that is less than about 10 cm on each side and less than about 1 cm in thickness. In comparison, free space optical instruments are generally more than 10 times and usually more than 100 times larger. The OIC provides a stable optical guiding platform with respect to temperature and mechanical vibration. The design and fabrication of the optical circuit controls the optical alignment and stability with high reliability.

The enhanced sensitivity of the SPR systems of the present invention derives, in part, from the ability to use a wavelength scan to detect the point of minimum reflection, the SPR signal, mitigating/eliminating the need for mechanical movement and with a stable optical path. The OIC enables the optical signal to be confined to the planar waveguides from the source to the detector, where the incident (and reflectance) angle to the SPR surface is defined by the integrated waveguide geometry. The OIC can include an AWG that functions as a wavelength selective element. The AWG, depending on the specific design, can have a wavelength resolution of better than about one Angstrom. The SPR signal can than be sampled at multiple wavelengths along the SPR minimum. In one embodiment, AWGs can be made with more than about 500 channels, and high resolution. In another embodiment, AWGs can be made with more than about 1000 channels, and high resolution. In yet another embodiment, AWGs can be made with more than about 2000 channels, and high resolution.

The detection limit, sensitivity of the SPR signal, is related to the resolution of the SPR minimum and line profile. The AWG, or other dispersive element in the OIC such as an integrated grating, provides the high resolution in a small size with high stability. This high resolution leads to index measurement sensitivity of better than about 1 part in $10^7$ when using an OIC with a 4 Å resolution and 800 Å wavelength range. The OIC enables the design and operation of an SPR instrument with extraordinary sensitivity compared to conventional free space methods.

The sensitivity in index measurement is directly related to the measurement sensitivity of SPR for molecules. In one embodiment, the about $1 \times 10^7$ or more index sensitivity translates to detection of molecules with a mass of less than about 750 Daltons at less than about 50% coverage. In another embodiment, the about $1 \times 10^7$ or more index sensitivity translates to detection of molecules with a mass of less than about 500 Daltons at less than about 50% coverage. Even higher molecular sensitivity can be achieved with a design that allows detection sensitivity for about 10% or less coverage.

The SPR systems of the present invention facilitate monitoring and measuring protein interactions. Proteins are large molecules with molecular masses in the range of thousands of Daltons. Such a large mass can lead to a large change of index. However partial coverage of the SPR surface is frequently the case and the high sensitivity of the SPR systems of the present invention allows the detection of low coverage. In a kinetic measurement, the rate sensitivity is dependent on the initial low coverage range. The high sensitivity enables more accurate kinetic measurement rates for protein binding.

The use of OICs in the SPR systems of the present invention allows enhanced dynamic range to be achieved along with the enhanced sensitivity as described above. A large change in sample refractive index (or thickness) shifts the point of minimum reflectivity outside of the wavelength range for the initial linewidth of the SPR signal. The AWG that is used, for example, in one embodiment, has a high sensitivity but also has a wide dynamic range. The AWG works in a high defractive order, typically higher than about 50. Also associated with the design is the free spectral range that gives the scanning range for a single high resolution scan. By coupling an appropriate wavelength source to a different input waveguide a different diffractive order may be used. Consequently, the same high resolution can be obtained in a separated wavelength channel. As an example, by shifting the wavelength source by 150 nm, the same resolution of about $1 \times 10^{-7}$ index or more can be obtained even though the index has changed by about 0.05. In one embodiment, the dynamic range for measurement is thus at least about 1:500,000 in index. In another embodiment, the dynamic range for measurement is thus at least about 1:500,000,000 in index. With such a dynamic range, index changes smaller than about $1 \times 10^7$ in index can be distinguished.

The SPR systems of the present invention facilitate nonspecific background (NSB) rejection. Another aspect of the invention relates to a method analyzing distribution in a Z direction and orientation of mass relative to a planar or graded (continuous or not continuous) SPR surface using at least one of multiple wavelengths, physical surface modification, depth profiling, and polarization analysis. The Z direction is normal to the SPR surface. The method permits the evaluation of specific binding versus nonspecific absorption and concentration and binding profiles of specifically bound mass.

The SPR systems of the present invention facilitate depth profiling. Any suitable wavelength of light may be employed, although visible light and infrared light are particularly useful. Visible light has a wavelength from about 390 nm to about 700 nm. Infrared light as used herein means light having a wavelength from about 700 nm to about 2500 nm. In one embodiment, the light employed has a wavelength from about 390 nm to about 2,500 nm. In another embodiment, the light employed has a wavelength from about 1,000 nm to about 2,000 nm. In yet another embodiment, the light employed has a wavelength from about 1,200 nm to about 1,850 nm. At longer wavelengths, higher penetration into the assay medium is achievable. Moreover, at longer wavelengths, the SPR is much sharper (meaning having a much smaller range of wavelength where the effect can be detected) than at shorter wavelengths; thus, SPR measurements at longer wavelengths leads to improved accuracy and improved sensitivity. When employing a microwell array made of silicon based materials, an additional advantage is achieved in that glass or plastic transparent supports are unnecessary as silicon and silicon nitride are transparent at longer wavelengths (such as over 1200 nm). Silicon based microwell arrays constitute disposable, solid state readily processable supports for bioanalysis. The flatness and precision of silicon based arrays relative to plastic is a significant advantage in making SPR measurements with high precision.

The SPR systems of the present invention facilitate improved sensitivity at longer wavelengths (such as about 1,000 nm or more). The SPR angle is dependent on wavelength. The penetration depth of the optical field is also dependent on the wavelength, with the longer wavelength penetrating further. The use of multiple wavelengths leads to a method of determining the difference between the bound and nonbound molecules. A further way of distinguishing between bound and unbound molecules is to compare the SPR signal with the TIR signal. The TIR angle, or wavelength at a specific angle, is sensitive to the index of the analyte, but the optical field penetrates further into the medium to give the index of the bulk analyte solution.

The SPR systems of the present invention facilitate detection of bound non-spherically shaped analytes, due to the ability to analyze the birefringence profile. Most analyte molecules such as proteins, DNA, RNA, sugars, and other molecules, are not spherical in shape. Bound ellipsoids have a different index for polarization perpendicular to or parallel to the long axis of the molecule. The polarization detection of the SPR systems of the present invention leads to a method to distinguish between bonded and nonbonded molecules. In particular, non bonded molecules generally have a random orientation and do not have birefringence whereas bonded molecules generally have a detectable orientational birefringence.

The SPR systems of the present invention can use light polarization to facilitate analyzing the bonding site between the analyte and receptor and/or the relative orientation between MBPs when bound. Linear birefringence is a difference of refractive index for two different linear polarizations propagating in a specific direction. For example, proteins are frequently anisotropic in shape. When an anisotropic material is bonded to a surface the ensemble is linearly birefringent due to the shape factor. The difference in index, birefringence of the bonded molecules for SPR can be detected and provides useful information for the analysis of the bonding site and orientation. Commonly, SPR is done for a single polarization, but it is possible to analyze both polarizations using a proper configuration described hereinafter.

Another aspect of the invention relates to a disposable microwell array for the bioanalysis system, such as the SPR system, containing a silicon substrate having an insulation layer formed thereover; a plurality of wells formed on a top surface of the silicon substrate and insulation layer; and a metallic layer on the silicon substrate within each of the wells. A first member of a binding pair may be attached to the metallic layer in some cases with appropriate intermediate linking layers while a second member of a binding pair is contacted with the first member simply by exposure to a sample solution. A glass or plastic substrate may be employed in place of the silicon substrate.

Another aspect of the invention relates to a disposable protein chip array for the bioanalysis system, such as the SPR system, containing a silicon substrate having an insulation layer formed thereover, and suitable chemistries for attachment on the surface. A first member of a binding pair may be attached to the metallic layer in some cases with appropriate intermediate linking layers while a second member of a binding pair is contacted with the first member simply by exposure to a sample solution. A glass or plastic substrate may be employed in place of the silicon substrate.

There are several configurations that provide mode matching from a glass to the metal in the SPR condition. In one configuration, an SPR bioanalysis system has the Kretschmann configuration, the metal is in contact with the high index glass and the analyte is in contact with the metal on the side away from the glass, glass-metal film-low index material. Another is an SPR bioanalysis system having the Otto configuration. In this case there is a thin air gap between the metal and the glass, glass-air-metal film-low index material. A third geometry for the SPR bioanalysis system is the Sarid configuration, where the metal film is between two low index materials; that is, glass-low index material-metal film-low index material. More sophisticated extensions of such a geometry can also be applied to significantly extend the range of surface plasmons that can be coupled to practical optical inputs. By placing on one or both sides of the metal films additional films or other structures with features (i.e., film thickness and/or lithographic patterns) much smaller than the wavelength of the incident light, an 'artificial dielectric' medium (more recently called 'photonic crystals') is created against the metal film. With proper design of the physical geometry of this nanostructured composite, the artificial dielectric behaves like a homogenous medium with an optical index of refraction that is much different than any of the indices of refraction of the component materials. Indeed, an artificial dielectric can have an apparent index of refraction that is numerically beyond the range of any real material. By using a properly designed artificial dielectric as the incident medium for the optical signal, the optical signal can be coupled to surface plasmons of either polarization and on a wider range of metals than are accessible through an homogenous adjacent medium. This can be used too glean information as to the distribution and alignment of molecules proximal to the plasmon.

This last configuration can be particularly useful for generating long range surface plasmons (LRSP). In some instances, the LRSP condition gives a much sharper resonance than the other configurations and provides an enhanced sensitivity. The SPR condition is polarization dependent in the glass-metal-low index material configuration that is most common. Modification of the geometry with an additional low index film between the metal and the analyte enables both s and p polarizations to couple to the metal. In this connection, U.S. Pat. No. 5,991,488 is hereby incorporated by reference.

Another configuration for the SPR geometry for the SPR bioanalysis system is the glass-low index material-metal film-low index material, where the low index material has a thickness from about 10 nm to about 100 nm and an index range from about 1.3 to about 2.2. This geometry facilitates the enhanced sensitivity of the long range surface plasmons with the sample birefringence detection.

The blanking schemes as described herein can be practiced at a gross level by moving light beams from assay well to assay well. The schemes can also be applied if active and inactive locations within a well are patterned within a well since this gives a better quality blank (all experimental variables are the same except the activity of the receptor). Use of multiple locations also can improve precision in assays by allowing averaging and identification of anomalous readings from identified locations. A 2×N switch OIC facilitates delivering light to multiple locations within a well on an SPR support.

The ability of PLCs to locate and spectrally analyze light beams with greater accuracy and precision than conventional light sources enables chemical multiplexing within each single assay well of an SPR support. By analogy with the blanking schemes outlined above, many different specific receptors can be arrayed within a single assay location (well) in, for example, an SPR disposable device. Receptors can be arrayed on a support made from one or more of (1) a constant thickness of a single metal, (2) a substrate made with varying thickness of a single metal and (3) from several different metals. The SPR signal is a function of metal identity and thickness and responds to analyte specific binding. Deconvolution of the SPR signal by physical location, wavelength and angle allows multiplexed assays to be conducted.

Sample supports (substrates) for bioassays may be disposable or re-useable. To facilitate performance of multiple assays, Microtiter plates (MTPs) are often used. These are physical arrays of small wells usually set out in a rectangular fashion and integrated into a flat plate typically made of plastic (glass, silicon, or silica may also be employed). The wells are usually open ended so that small volumes of liquids (<$\mu$L of samples and reagents) can be dispensed into them. The MTPs are used to incubate assay reactions and permit evaluation of the assay by the bioanalysis systems of the present invention optionally with the assistance of an optical instrument called a Microtiter plate reader.

In one specific embodiment, an MTP has an array of 12×8 wells for a total of 96 wells each having a capacity of about 0.2 $\mu$L. Other MTPs may have, for example, 24×16 (384 wells) and 48×32 (1536 wells) well arrays. MTPs having standard well locations and geometries are established and can be used by existing detectors and dispensers. The physical form and other functionally important characteristics of well based assay formats are subject to standards set by convention. One such set of standards set forth by the Society for Biomolecular Screening (SBS) is known as SPB standards. One aspect of this design involves configuring a disposable made of plastic, glass, silicon, etc. using this format to meet SBS standards.

In one embodiment, the support or substrate for the SPR bioanalysis contains assays or wells where each has a volume of about 0.5 $\mu$L or less. In another embodiment, the support or substrate for the SPR bioanalysis contains assays or wells where each has a volume of about 0.2 $\mu$L or less. In yet another embodiment, the support or substrate for the SPR bioanalysis contains assays or wells where each has a volume of about 0.05 $\mu$L or less.

In one embodiment, the support or substrate for the SPR bioanalysis system is a gene chip, DNA chip, or proteome chip. Gene chips typically include a glass slide spotted with rows of nanoliter sized dots of genetic material. Analogous to a DNA chip, proteome chips carry thousands of nanoliter sized dots of proteins (each having at least one MBP), primed to react with any compound of interest (the other MBP) for which binding information is sought. Chips or microarrays can carry anywhere from about 100 to about 50,000 protein 'capture' molecules (one MBP), each capable of identification of one particular protein (the other MBP). Protein microarrays are capable of identifying a large number of proteins in a sample and quantifying how much of each protein is present. This type of high throughput chip allows one to determine which proteins of a gene are expressed in a sample, and enables one to gather higher multiplicity protein profiles from patients.

In one embodiment, the support or substrate for the SPR bioanalysis system is a microarray material. In contrast to traditional hybridization assays that utilize flexible membranes such as nitrocellulose and nylon, radioactivity, and autoradiography, a traditional microarray or biochip assays utilize solid surfaces such as glass with fluorescent labeling and detection. One advantage of the chip format is that the solid surface is non-porous and thus enables the deposition of small amounts of biochemical material in a precisely defined location. Porous substrates such as nylon and nitrocellulose allow diffusion of applied materials. A non-porous substrate also prevents the absorption of reagents and sample into the substrate matrix, allowing the rapid removal of organic and fluorescent compounds during biochip fabrication and use. A non-porous surface permits the use of small sample volumes enabling high sample concentrations and rapid hybridization kinetics that increases the quality of the array elements. The inherent flatness of the microarray format permits true parallelism, which is lacking in all filter based assays. Parallel analysis provides a significant increase in the accuracy of the assay data. Metalization is straightforward and can be achieved with excellent tolerances and uniformity.

There are many manners in which to fabricate the supports. The biochip format is compatible with many advanced fabrication technologies and is thus amenable to automated manufacture. The three primary technologies used presently in microarray manufacture include photolithography, ink jetting and mechanical microspotting. Each technology has specific advantages and disadvantages, though none of these technologies is compatible with the nonporous substrates used in traditional hybridization assays.

Using photolithography relies on the use of semiconductor technologies in a biochip setting. The piezoelectric technologies utilize version of 'ink jet' printing to dispense sub-nanoliter volumes of reagent to defined locations. Electricity is used to deliver molecules via tiny delivery jets onto a solid surface. An XYZ motion control system directs the location of the jets during this noncontact printing process. The microspotting technologies rely on direct surface contact for microarray fabrication. A printhead containing microspotting pins, capillaries, or tweezers allow transfer of pre-made substances from reagent trays onto solid surfaces. An XYZ motion control system directs the preparation of microarrays of biomolecules.

These technologies each provide sufficient density to provide single chip that can represent a portion, substantial portion, or even the entire human genome. The variable requirements of throughput, density, cost quality, flexibility, and other criteria dictate the use of one of these technologies in a given setting. An alternative is to produce protein arrays in a floppy disk sized microcard format that uses tiny channels allowing only one way flow. A syringe can be used to load the sample manually.

MEMS (micro-electrical mechanical systems) can also be used to manufacture the supports. MEMS can be manufactured using silicon, glass, polymers, and other materials. Microsystems may be constructed from parts produced using different technologies on different substrates, connected together; i.e. a hybrid system. For example, a silicon chip can be used to implement control circuitry, whereas the actuators it controls can be micromolded in plastic, or electroplated metal (using the LIGA technique, for instance). Alternatively, components of a system may be constructed on a single substrate using one technology (a monolithic system). Hybrid systems have the advantages that the most appropriate technology for each component can be selected to optimize system performance. This can lead to a shorter development time since microfabrication techniques for each component may already exist, and compromises may not have to be made to ensure that each component can be fabricated without damaging components already existing on the substrate. Monolithic devices typically are more compact than hybrid devices, and more reliable (fewer interconnections that can go wrong, for example).

Metalization of the support may be performed in any suitable manner. In one embodiment, the SPR substrates are glass slides coated with gold and then derivatized with a self assembled monolayer or a dextran type matrix. Planar metal surfaces made by highly uniform thin films of noble metals formed by magnetron sputter deposition, evaporation or other techniques onto plane glass, polymer, or ceramic substrate plates are used. These plates are precision diced to produce substrates formed from deposited gold or platinum (for example, having a thickness from about 50 Å to about 5,000 Å, such as about 1,000 Å). The metal films can be optionally deposited over an adhesion promoting layer of titanium-tungsten (for example having a thickness from about 50 Å to about 500 Å) (often termed an adhesion alloy). The metal is deposited onto a substrate, such as a very smooth (for example, 60/40 scratch and dig finish), highly insulating, chemically resistant and nonleaching, electronics grade borosilicate glass substrate. Substrates such as plastic, glass, silicon, with an oxidized silicon or silicon nitride insulating layer, can also be employed.

A support may be fabricated as a protein chip and microtiter format. Most arrays are created on glass or silicon slides-standard in the production of DNA microarrays-treated with an aldehyde moiety or other agent to immobilize the protein. Other materials investigated as immobilizing coatings include layers of aluminum or gold, hydrophilic polymers, and polyacrylamide gels. Each material demands its own chemistries (which must avoid denaturing the protein molecules) ideally to orient each molecule in the same direction while at the same time creating a hydrophilic environment in which reactions can take place.

For example, suitable chips include those manufactured by Zyomyx (Hayward, Calif.), use photolithography to etch miniature wells on the surface of silicon chips. The immobilized proteins or antibodies are located in the flow chambers on the chip.

Other suitable chips include those manufactured by Large Scale Biology (Vacaville, Calif.). Hundreds of thin plastic rods, each doped with a particular antibody, are bundled together in a sheaf. The sheaf is then cut transversely into micrometer thin slices, yielding chips containing antibody loaded plastic circles (the rods' cross-sections). A meter long sheaf could generate a million low density chips, each with ten to a few hundred elements potentially a high volume, low cost product.

Still other suitable chips include those manufactured by Packard BioScience Company uses hydrogel chip substrates where proteins are imprinted on a porous polyacrylamide gel, similar to that used in electrophoresis, and immobilized using a coupling reagent that forms a covalent bond with amine groups on the protein molecules. The gel is aqueous, so immobilized proteins can undergo binding reactions in solution.

Examples of substrate or support material for any of the above mentioned formats include silicon, silica, plastics, glass, or other dielectric or semiconductive substrate material. Many the techniques required to make substrates can be derived from the semiconductor industry and are based on silicon processing and materials. There are basic techniques associated with silicon micromachining. These are the deposition of thin films of materials, the removal of material (patterning) by wet chemical etchants, and the removal of material by dry etching techniques. Photolithography is the basic technique used to define the shape of micromachined structures in the techniques outlined below, but any patterning technique including maskless lithography can be employed. The technique is essentially the same as that used in the microelectronics industry.

There are a number of basic techniques that can be used to pattern thin films that have been deposited on a silicon wafer, and to shape the wafer itself, to form a set of basic microstructures (bulk silicon micromachining). The techniques for depositing and patterning thin films can be used to produce quite complex microstructures on the surface of silicon wafer (surface silicon micromachining). Electrochemical etching techniques can be employed to extend the set of basic silicon micromachining techniques. Silicon bonding techniques can also be utilized to extend the structures produced by silicon micromachining techniques into multilayer structures.

Typical plastics used for microtiter plates are thermoplastics, those retaining the ability to flow at elevated temperatures for relatively long time periods. Key plastic design considerations include the softening point (glass transition temperature) of the material, stability of the material to temperature, oxidation, etc. and the product requirements. Engineering thermoplastics can be defined with a unique combination of properties. For example, high purity materials with excellent transparency (low absorption/scattering), low density, high heat deflection temperatures, high dimensional stability, and excellent electrical properties may be obtained using commercially available materials. Additionally, water vapor barrier properties and low moisture absorption can be obtained in materials that flow well and shrink and warp little during injection molding.

Plastic parts can be made by techniques that can be inexpensive and fast in high volumes. Conversely, substrates made from inorganic materials, on the order of 100 cm$^2$ required for DNA sequencing or pharmaceutical candidate screening, which require drilling and sealing processes can be quite cumbersome to fabricate. Plastic substrates can be made so cheaply as to be disposable after a single use. This is advantageous in applications where cross contamination of sequential samples is of concern. The high throughput screening of candidate pharmaceutical libraries and genotyping for forensic identification are two instances where contamination of one sample by another is most undesirable.

Flow cell measurements on the supports involve a bulk or microfluidic interface to the active optical element. Analyte is allowed to pass over the sensor surface in a continuous and controlled flow or pulsed flow, preferably maintaining substantially constant analyte concentrations at the sensor chip surface. The benefits of a microfluidics system are low sample consumption and minimization of sample volume. The microfluidics system may permit certain types of blanking schemes. The advantage of a flow system is increased accuracy of kinetic and concentration analysis data. For example, an SPR detector having collector for eluted ligand uses a microfluidic cartridge with a drain port; comprised of an injection port, an open channel, a drain port in communication all in communication. U.S. Pat. No. 5,395,587 describes such a flow system, and is incorporated herein by reference for such systems.

SPR bioanalysis systems may utilize microfabricated channels. In one specific embodiment, the SPR bioanalysis system uses a patterned photobiotin probe in microfluidic channels for sensing proteins with SPR. SPR bioanalysis systems may use microfluidics and surface chemistry to follow biospecific interactions.

In one embodiment, a silicon based standard microlithography processing is employed to make single use disposable supports. For example, a 2D array of microwell patterns on about 2.25 mm centers is laid out and diced from a wafer to make up to 1536 wells or well arrays (size just under about 3 inches). This layout is compatible with commercially available microdispensers, which are designed with a single dispense heads on either 9 mm, 4.5 mm, or 2.25 mm spacing (for 96, 384, and 1536 well plates, respectively). Metalization of the wells (required for SPR) and attachment of receptors (antibodies and the like) involve employing known, inexpensive processes.

When using OICs in an SPR system, the use of monocrystalline silicon as an alternative to plastic or glass in the SPR support is facilitated. Relative to plastics, increased flexibility in the choice of metallic supports on which assay specific chemistry occurs is thereby achieved due to a generally wider latitude in thermal and chemical deposition and processing conditions. The OICs may additionally be produced using standard MEMS devices and techniques. Microlithography and microfabrication developed for standard MEMS semiconductor processing can be used.

In one embodiment, the OIC device is designed to work in the wavelength range from about 1300 nm to about 1650 nm using single mode waveguides. The index and dimensions are different for other wavelengths. The OIC starts with a silicon substrate or wafer. The silicon wafer is the type commonly used in fabrication of silicon based integrated circuits. The processes used here are also similar to those used in the fabrication of silicon integrated circuits. For example, a lower cladding layer of silica is formed on the substrate, such as grown by thermal oxidation or deposited by PECVD (Plasma Enhanced Chemical Vapor Deposition). The PECVD process and equipment is similar to that used in fabricating integrated circuits. This lower cladding layer is at least about 20 μm thick to ensure that the optical field in the core is not attenuated by the silicon.

The core layer is next deposited and lithographically defined. A core layer of doped silica, doped for example with germania, is next deposited by PECVD. The doping increases the refractive index above that of pure silica. The index of the core layer is from about 0.25% to about 2%, such as from about 0.4% to about 1%, above that of the pure silica. The thickness of the doped core layer is typically from about 1 μm to about 25 μm, the thinner layer being used for the higher doping concentrations. In another embodiment, thickness of the core layer is typically from about 4 μm to about 8 μm. The core layer may also have co-dopants, such as one or more of boron and phosphorus oxides to control the stresses caused by different coefficients of thermal expansion for the different materials in the device.

The core layer is then patterned with the waveguide circuit design by known micro fabrication lithography processes. A thin layer of amorphous silicon is deposited onto the core to serve as a hard mask. Photoresist is spin coated and imaged using photomask technology, standard in microfabrication, with the specific device pattern. The photoresist is then developed and the silicon hard mask is etched by either standard wet processes or by standard dry (plasma) processes. The photoresist is then removed. The patterned core layer on the silicon wafer is then etched in plasma etching equipment standard in the fabrication of integrated circuits. The plasma process removes the doped silica from the regions that are not covered by the silicon hard mask. The etching is complete when the core layer is etched to the bottom clad layer. The hard mask is then removed by standard processes.

The top clad layer is then deposited by PECVD. The top core layer has an index the same as the bottom clad layer. The top clad layer is typically doped with boron and phosphorous oxides to lower the melting point below that of silica or the core material. The top clad layer is typically at least about 20 μm thick.

An additional step for the fabrication of optical switches is the deposition of the switching electrodes. The optical switches described here are based on the thermo-optic effect. That is, the switching occurs due to the change of index from the change in temperature in the waveguide region caused by a local heater. The heater is typically made from a thin film metal resistor on top of the cladding over the core region. Typical thin film heaters are made from refractory metals such as tungsten, titanium or tantalum. The metal is deposited on the top clad of the OIC wafer by sputtering or evaporating in the normal process used for metal deposition in semiconductor processes. Sometimes plating is used to increase the thickness of the metal. Standard patterning methods are used for the metal circuit definition: photoresist coating, expose the resist through a photomask, develop the resist, etch the metal and strip the resist.

When the wafer fabrication is complete the wafer is diced into individual OIC devices. After optional optical testing, the OIC devices are assembled and packaged as necessary for the final application. In the case described in FIG. 7, the optical fibers connected to laser diodes are attached to the OIC and a detector is assembled to the device. Additional optical coupling elements are assembled to bring the light to the SPR cell and to return the reflected light to the OIC.

Generally, the applications of the OIC in the bioanalysis systems involves detecting and/or measuring index changes in analyte. The practical consequence of this interaction is that the concentrations of specific molecules can be quantitatively measured by observing the SPR shifts that occur when the molecules bind to the surface of a support sensor. In a support sensor, a gold (or other metal) surface is coated with a MBP which may be antibodies, DNA probes, enzymes or other reagents chosen because they interact exclusively with a selected target, analyte or molecule. When the support sensor is exposed to a sample that contains analyte molecules, they bind to the sensor's surface via their specific interaction with the surface attached MBP. Over a range of solution concentration that typically begins at zero and extends to within approximately at least 50% of the concentration at which all the surface-attached MIPs are occupied by molecules from solution, the amount of binding that occurs is proportional to the concentration of the analyte in the sample solution. This binding event changes the composition of the medium at the surface and produces a SPR shift. The magnitude of the shift is typically proportional to the amount of binding that takes place, in particular when there are no strong interactions between adjacent bound molecules and when the extent of binding is less than approximately 50% of the saturation occupancy of the binding layer. Comparison of the observed SPR shift with a stored calibration curve yields a quantitative measurement of the concentration of the analyte in the sample.

The phenomenon of SPR is non-specific. It cannot per se distinguish between different chemical changes. While this may appear to be a limitation, it is really a powerful advantage. Specificity depends upon selection of pairs of molecules that react only with each other. One member of the pair is the detector and the other is the target analyte (i.e. the substance to detect/quantitate). Any pair of molecules that exhibit specific binding can be adapted to SPR measurement.

For example, an SPR binding event may occur as follows. In an immunoassay a thin film of metal is applied to a surface (typically glass or plastic). The metal film can be from about 35 nm to about 200 nm thick. Then antibodies specific to a particular analyte (e.g. hormone, drug, tumor marker, etc.) are chemically attached to the metal film. When the sensor is exposed to a sample containing that analyte, the binding of the antibody and the analyte causes a change at the metal surface, within the plasmon field, and the shift in the resonant wavelength of the incident light is measured. The size of the shift is typically proportional to the quantity of the analyte in the sample if the interaction is allowed to reach chemical equilibrium and if the amount of analyte bound at equilibrium is less than approximately 50% of the amount required to interact with every antibody. Because of the very specific relationship between the antibody and analyte, no other molecule in the sample can be mistakenly measured by the detector/sensor provided that substantially no other molecule adsorbs or binds "nonspecifically".

The surface plasmon is affected by changes in the dielectric value of the material in contact with the metallic support. When a first MBP is immobilized on the metallic support of an SPR system, and a solution containing a second MBP with specificity for the first MBP is contacted with the metallic support, a binding event occurs between the first and second MBPs. The binding event results in a change in the dielectric value and/or physical thickness of the material in contact with the metallic support. This change is monitored/detected by the light detector. The light detector may be or include an OIC. The light detector may be or include a reflectance spectrophotometer or a mass spectrometer.

Index changes in analyte indicate specific surface binding. MBPs, as used herein, include "receptors", "ligands" and "analytes", and encompass a wide variety of molecules ranging from small molecules to large proteins and polynucleotides, as well as a variety of interaction pairs. Examples of MBPs include the agents listed below (representative interaction partners are parenthetically identified): antigen (specific antibody), antibody (antigen), hormone (hormone receptor), hormone receptor (hormone), polynucleotide (complementary polynucleotide), avidin or streptavidin (biotin), biotin (avidin or streptavidin), enzyme (enzyme substrate or inhibitor), enzyme substrate or inhibitor (enzyme), lectins (specific carboxyhydrate), specific carboxyhydrate (lectins), lipids (lipid binding proteins or membrane associated proteins), lipid binding proteins or membrane associated proteins (lipids), polynucleotides (polynucleotide binding proteins), polynucleotide binding proteins (polynucleotides), receptor (transmitter), transmitter (receptor), drug (target), target (drug), as well as more general types of interactions such as protein (protein), protein (polynucleotide), polynucleotide (protein), small molecule (protein), protein (small molecule), enzyme (small molecule), receptor (small molecule), polypeptide (small molecule), polynucleic acid (small molecule), DNA (DNA), DNA (RNA), and RNA (DNA) interactions.

As used herein, the term "binding event" includes dissociation kinetic parameters and association kinetic parameters as well as the steady state aspects of the binding interaction between the MBPs, such as between a ligand and analyte of interest (e.g., affinity or avidity). Binding events thus include association rate, analyte surface concentration at steady state, dissociation rate, and regeneration effect, all of which may be measured. The measured binding event may then be compared with a set of predetermined characterizations of other test molecules so as to provide valuable information concerning the potential activity or functionality of the MBPs.

Assays generally suffer problems due to signal generation due to nonspecific binding. In SPR, this is a concern since any matter binding to the solid phase can be confused with an analyte specific signal. Blanking is a method that is routinely used in biochemical assays. In this method, a signal corresponding to no-analyte or no active receptor is measured and subtracted from the assay specific signal. In the SPR system of the present invention, a PLC light switching component permits rapid measuring of the differential signal (specific versus non specific) taking advantage of rapid switching in the time domain and accurate light beam steering in the x-y domain of the SPR device. This consequently permits two types of blanking: static (difference in a signal to no-analyte or no active receptor and the assay specific signal after equilibrium) and kinetic, which permits distinguishing (typically) rapid nonspecific binding from slower specific binding.

Blanking using regularly spaced replicate assay locations: by placing multiple assay locations at defined locations and/or alternating positive and negative assay responses (assay receptor/physically equivalent not-active material (e.g. antibody/non-immune IgG)), frequency modulation can be used to pull out an assay specific signal from a large nonspecific background if present. Light may be routed to many locations on an SPR support in a rapid raster and the assay specific signal is that fluctuating at the appropriate frequency.

Temperature-jumping is a powerful method for investigating binding interactions with the SPR systems and methods of the present invention. Changing temperature can perturb a chemical system at equilibrium. As the system relaxes to a new equilibrium fresh information is obtained as to the kinetics and equilibrium involved. Rapid changes in temperature permit evaluation of processes that occur quickly. For example, many processes of interest in protein-:protein interactions occur in the millisecond time range. SPR disposables can have low thermal mass so that rapid temperature jump conditions are facilitated. Local heating can be achieved in a variety of ways (including passing electric current through the metal film) so that many reactions can be evaluated simultaneously.

OICs permit control over the intensity and wavelength of light directed at the SPR support, thereby permitting control over varying penetration depths of light into the array medium. This feature contributes to the ability to distinguish between non-specific binding and specific binding, since specific binding occurs at discrete depths while non-specific binding occurs at multiple depths.

OICs permit the SPR system to selectively deconvolute an SPR signal (by location, wavelength, time, and/or angle). AWGs for example permit the delivery of certain discrete wavelengths of light at the SPR support, thereby decreasing noise or non-specific background signals. OICs that analyze fine changes in SPR wavelength and can extract an SPR signal from a large non-specific background.

OICs permit detection of small intensity changes, which provide improved sensitivity even in picomolar concentration ranges. The detection of small refraction changes also facilitates the detection of binding events involving small molecules, such as peptides and small entities made by chemical synthesis (such as a heterocyclic compound), which typically result in a smaller change in optical properties of the film of material on the metal surface than do the binding of larger molecules, e.g. proteins or nucleic acids. In one embodiment, small molecules have a molecular weight of about 2,000 or less. In another embodiment, small molecules have a molecular weight of about 1,500 or less.

Furthermore, OICs are sufficiently sensitive for making multiple detections over time to facilitate distinguishing relatively rapid non-specific binding from relatively slow specific binding in those cases where the kinetics of binding differ in such a manner. Using an OIC in the light detector enables at least about 5 times increase in resolution for the integrated thickness times index of refraction product compared with conventional detectors. In another embodiment, an OIC based light detector provides at least about 20 times increase in resolution for the integrated thickness times index of refraction product compared with conventional detectors. In yet another embodiment, an OIC based light detector provides at least about 50 times increase in resolution for the integrated thickness times index of refraction product compared with conventional detectors. In yet another embodiment, an OIC based light detector provides at least about 100 times increase in resolution for the integrated thickness times index of refraction product compared with conventional detectors.

OICs may take many forms, and have various elements of design, materials, AWG, switches, etc. An OIC is a planar device with optical waveguides. An optical waveguide is composed of a core region of higher index than the surrounding clad region. The propagating light is confined to the higher index region. The OIC described here are composed of silica based glasses for the core and cladding and are built on a silicon substrate. Other substrates for silica OICs include various high temperature glasses. Other material technologies that can be used include polymer core and cladding materials built on silicon, glass or polymer or semiconductors such as silicon or indium phosphide. OICs provide significant advantages over alternative methods of routing and manipulating light such as free space optics and individual fiber optic waveguides. The OICs provide small size, stability, low cost and the ability to integrate multiple functions in a single device with performance equal to or better than can be achieved in other configurations.

In one embodiment, the OIC contains an AWG. One advantage associated with AWGs is the improved performance of AWGs compared to other spectrometer designs such as the use of grating or prisms for the optical dispersion. AWGs are based on the principle of interferometry and perform the same wavelength dispersive function as a diffraction grating, but with some advantages. An AWG can function to combine different wavelengths of light into a single waveguide or with light propagating in the opposite direction to separate the multiple wavelengths into separate waveguides. The dispersive function is used to do the combining or separating of the wavelengths of light. AWGs can have a demultiplexing configuration or a multiplexing configuration. There are five basic elements of an AWG in the multiplexing configuration to combine multiple wavelengths into a single waveguide: 1) the input waveguides, 2) input focusing slab waveguide, 3) waveguide array, 4) output focusing slab waveguide, and 5) output waveguide.

In operation, the various wavelengths of light are each launched into a single mode waveguide, that then diffracts into the slab focusing region. The input waveguides are arranged on a circle. The far field of the diffracted light is a Gaussian pattern for each of the input wavelengths. This Gaussian pattern has a circular wavefront and the arrayed waveguide at the input side are on a circle. Every waveguide in the array is located on the circle with a substantially constant separation along the chord. This arrangement is the Rowland circle configuration. The circle of arrayed waveguides is centered at the junction between the central input waveguide and the slab waveguide. The waveguides are widened at the input to the slab to reduce coupling loss between the slab and the waveguide. The waveguides in the array are of a sufficient number to collect nearly all the diffracted optical power from the input waveguides. The waveguide array is the dispersive element and may have up to several hundred waveguides each with a different length, L, and ΔL is the optical path length difference. The order that the grating operates in is ΔL/λ, where λ is the center wavelength for the device. At the output of the array the optical power enters the output focusing slab where the light is focused onto the output waveguide. Since the light traversing the waveguide array experienced a wavelength dependent phase shift the light focusing is wavelength dependent and each wavelength is focused on the output waveguide. The output focusing slab is arranged on a Rowland circle, as is the input focusing slab. The multiple wavelengths are now on the single mode output waveguide.

In one embodiment, the OIC contains a thermo-optic switch. The optical switches used in this design are based on the thermo-optic effect. When materials are heated the index of refraction typically changes, that is, dn/dT (where is the ratio of the incremental change in index to an incremental change temperature) is not zero. The dn/dT of silica is positive in the temperature range around normal room temperature. For most other materials, such as polymers and semiconductors, dn/dT is negative. The propagation of light is dependent on the index of the material, a lower index leads to a higher propagation velocity. The difference in propagation velocity is used in the design of optical switches based on interference. A typical interferometric optical switch design is based on a Mach-Zehnder interferometer. The propagating light in the input waveguide is split into two equal parts in a Y splitter or directional coupler and each part propagates in a separate waveguide. The optical power is combined in a 2 by 2 coupler. The output path the light takes in this coupler depends on the phase relation between the optical power in each input waveguide that are the arms of the Mach-Zehnder interferometer. By introducing a phase delay in one of the optical paths relative to the other path the output switches from to the second output. The optical switch based on the thermo-optic effect uses heat to introduce a phase shift in one branch of the Mach-Zehnder and switch the light. The thin film heating element described above provides the change in index and thus in the light propagation in the heated arm relative to the waveguide that is not heated. The heater is designed to dissipate in the range from about 10 mW to about 300 mW of thermal power to provide a change in n of about $4 \times 10^{-4}$.

In one embodiment, the OIC contains one or more waveguide gratings. Waveguide gratings are used to couple light out of and into the waveguide. The grating can be designed to have a specific coupling angle for the light. Gratings can be made in a variety of ways such as photo-patterning of the completed waveguide with UV light or by etching a relief grating into the waveguide during fabrication. In the first method, short wavelength UV light, typically from about 190 nm to about 200 nm wavelength from an excimer laser is used to pattern the completed waveguide. The light passes through apertures in a metal mask designed for the specific design and then through the top cladding. The doped core of the waveguide is sensitive to the UV light with an increase of index in the irradiated regions. Irradiating a series of lines makes the waveguide diffraction grating transverse to the waveguide. The relief grating can be fabricated by etching the diffraction pattern into the bottom clad prior to the deposition of the core material.

The individual OIC optical components, such as the AWG and the thermo-optic switches, as well as splitters and other components can be connected by waveguides into many different configurations to perform specific circuit functions. The SPR analysis systems illustrated in FIGS. 3 to 7 incorporated OICs made by the methods described above.

Figure 3:
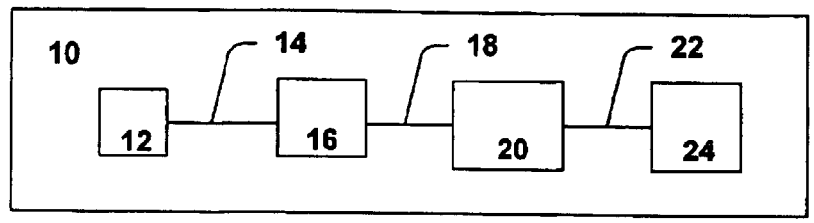
FIG. 3 illustrates a high level schematic view of a bioanalysis system in accordance with one aspect of the present invention.

Referring to FIG. 3, a high level schematic view of an SPR system 10 is shown. The SPR system 10 includes an illumination source 12, an OIC 16, an SPR metallic support 20, and an illumination collector 24. The illumination source 12, OIC 16, SPR metallic support 20, and light collector 24 are in communication via optical paths 14, 18, and 22. Optical paths 14, 18, and 22 may be optical fibers, or simply light generated by illumination source 12. The illumination source 12 is any suitable light source, such as a laser, that generates light that is subsequently incident on metallic support 20. OIC 16 may be a 2×N optical switch that facilitates directing light to specific location on metallic support 20. alternatively, OIC 16 may contain an arrayed waveguide grating spectrometer. Light reflected from the metallic support 20 is collected by the collector 24, which may be coupled to an analytical device such as a computer. The collector 24 may also contain an OIC.

Figure 4:
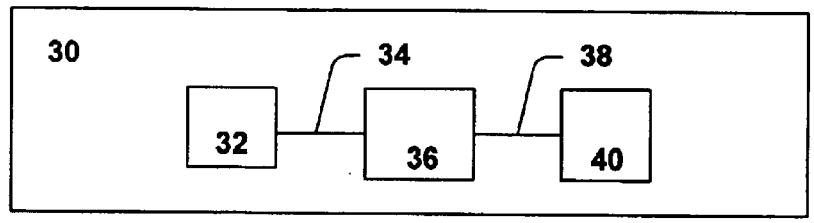
FIG. 4 illustrates a high level schematic view of another bioanalysis system in accordance with one aspect of the present invention.

Referring to FIG. 4, another high level schematic view of an SPR system 30 is shown. The SPR system 30 includes a light source 32, an SPR metallic support 36, and a light detector 40. The light source 32, SPR metallic support 36, and light detector 40 are in communication via light paths 34 and 38. Light paths 34 and 38 may be optical fibers, or simply light generated by light source 32. The light source 32 generates light that is subsequently incident on metallic support 36. Light reflected from the metallic support 36 is collected by the light detector 40, which is an OIC. In particular, light detector 40 may be an PLC containing an AWG and a detector array.

Figure 5:
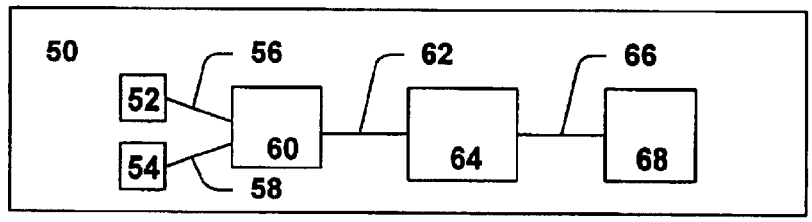
FIG. 5 illustrates a high level schematic view of an SPR system in accordance with one aspect of the present invention.

Referring to FIG. 5, yet another high level schematic view of an SPR system 50 is shown. The SPR system 50 includes a first light source 52, a second light source 54, an OIC 60, an SPR metallic support 64, and a light detector 68. The first light source 52, second light source 54, OIC 60, SPR metallic support 64, and light detector 68 are in communication via light paths 56, 58, 62, and 66. Light paths 56, 58, 62, and 66 may be optical fibers, or simply light generated by light sources 52 and 54. The light sources 52 and 54 are any suitable light sources that generate light which is subsequently incident on metallic support 64. OIC 60 may be a multiplexer that facilitates combining light from different light sources. Light reflected from the metallic support 64 is collected by the light detector 68. Light detector 68 may be a PLC containing an AWG and a detector array. OIC 60 may further contain a 2×N optical switch that facilitates directing light to specific location on metallic support 64.

Figure 6:
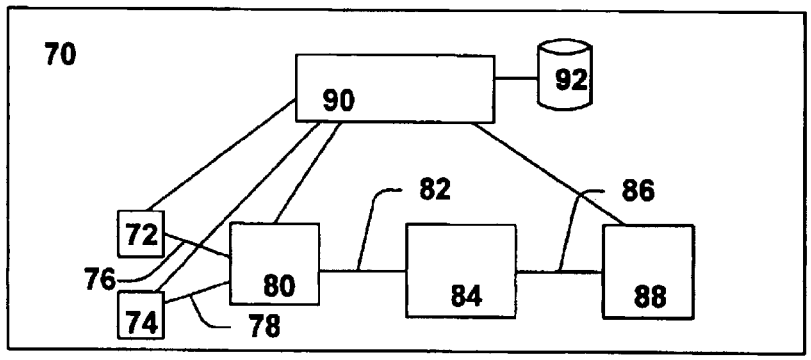
FIG. 6 illustrates a high level schematic view of a bioanalysis system with feedback control in accordance with one aspect of the present invention.

Referring to FIG. 6, a high level schematic view of an SPR system 70, having feedback control is shown. The SPR system 70 includes a first light source 72, a second light source 74, an OIC 80, an SPR metallic support 84, and a light detector 88. The first light source 72, second light source 74, OIC 80, SPR metallic support 84, and light detector 88 are in communication via light paths 76, 78, 82, and 86. The system further contains a processor controller 90 coupled to one or more of the light sources 72 and 74, the OIC(s) 80 and light detector 88. An optional memory store 92 may be coupled to the processor controller 90. The processor controller 90 may function to set or change various aspects of an SPR method, such as the type or intensity of light directed at the metallic support 84, the angle at which the light is directed at the metallic support 84, the manner in which the light detector 88 collects reflected light (particularly when the light detector contains an OIC), and the like. In this connection, the processor controller 90 send/receives signals to/from one or more of the light sources 72 and 74, the OIC(s) 80 and light detector 88. The processor controller 90 also may be coupled to servo-apparatus that changes the metallic support 84 when further assays are desired (not shown). The memory store 92 may contain data associated with previously monitored binding events, and this data may be compared with fresh data generated by the processor controller 90 and/or the light detector 88 in real time.

Figure 7:
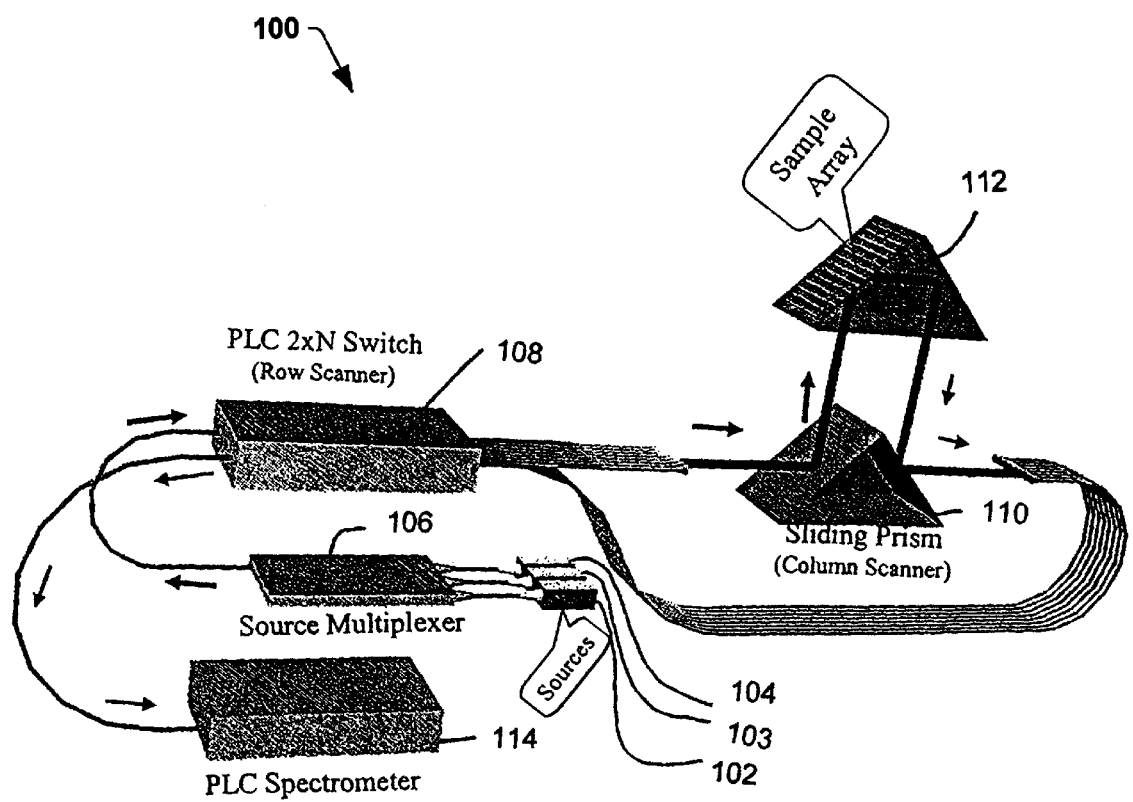
FIG. 7 illustrates a specific example of an SPR system in accordance with one aspect of the present invention.

Referring to FIG. 7, a specific example of an SPR system 100 is shown. The SPR system 100 includes lights sources 102, 103, and 104, an OIC 106 containing a PLC multiplexer, a second OIC 108 containing a PLC 2×N switch, a sliding prism 110, a sample array on a metallic support 112, and a PLC spectrometer 114 containing and AWG and detector array. The light sources 102–104, OIC 106, second OIC 108, and PLC spectrometer 114 are connected by optical fibers. Light is delivered from an optical fiber ribbon exiting the second OIC 108 to the metallic support 112 via a prism.

Figure 9:
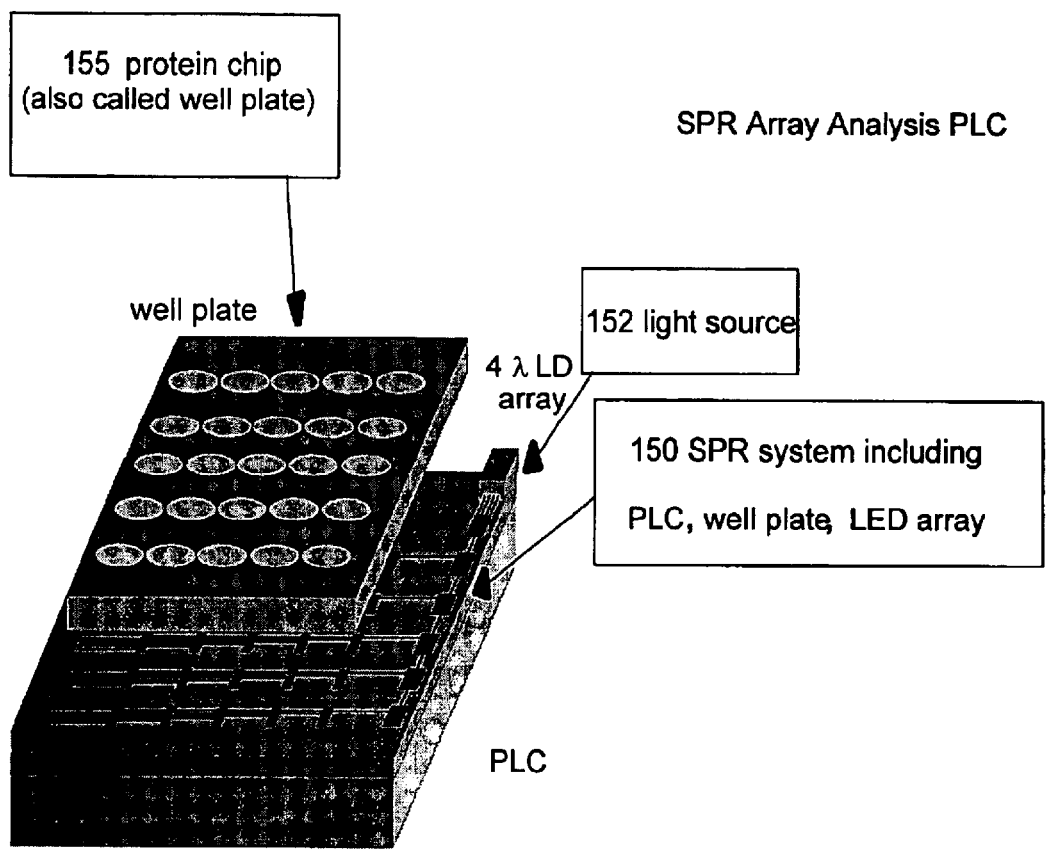
FIG. 9 illustrates an array assembly for an SPR system in accordance with one aspect of the present invention.
Figure 10:
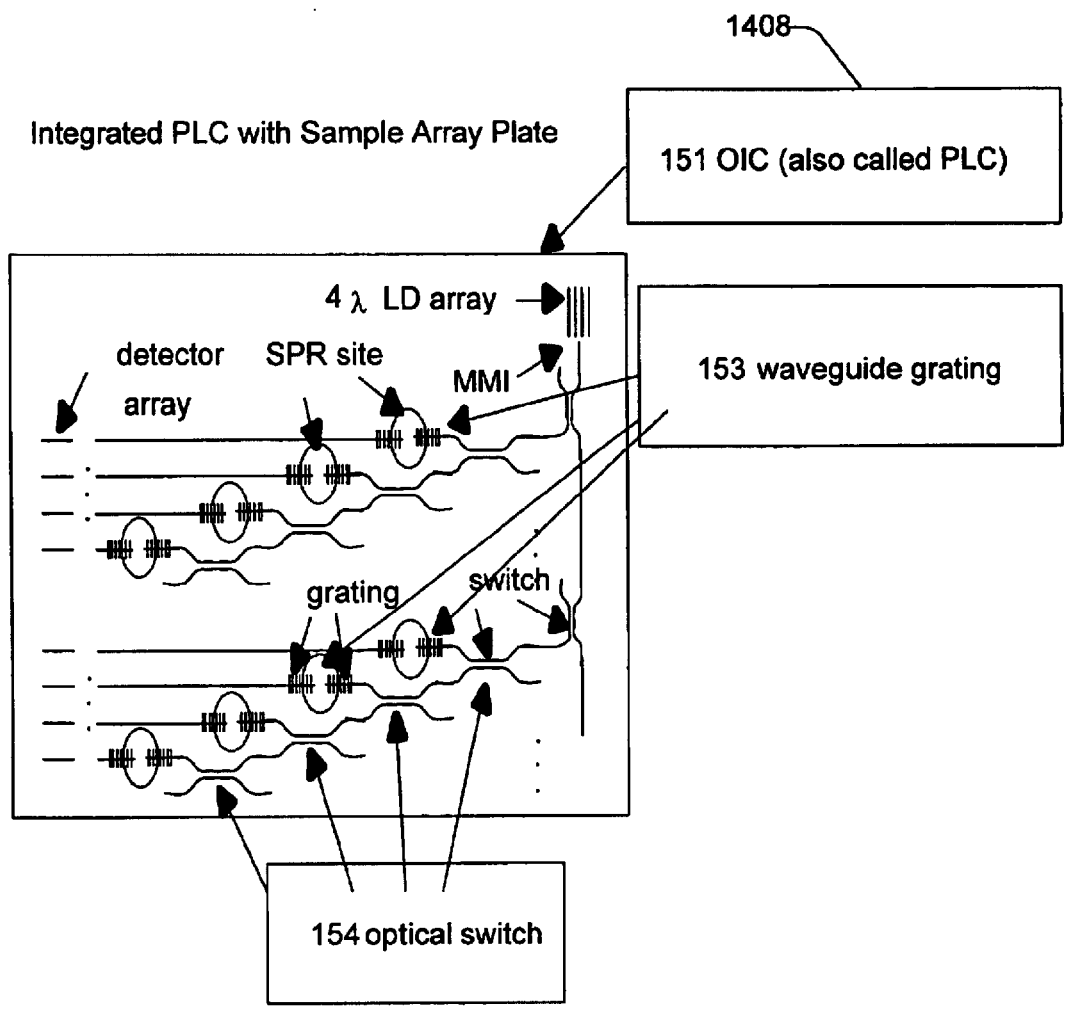
FIG. 10 illustrates an OIC for an SPR system in accordance with one aspect of the present invention.
Figure 11:
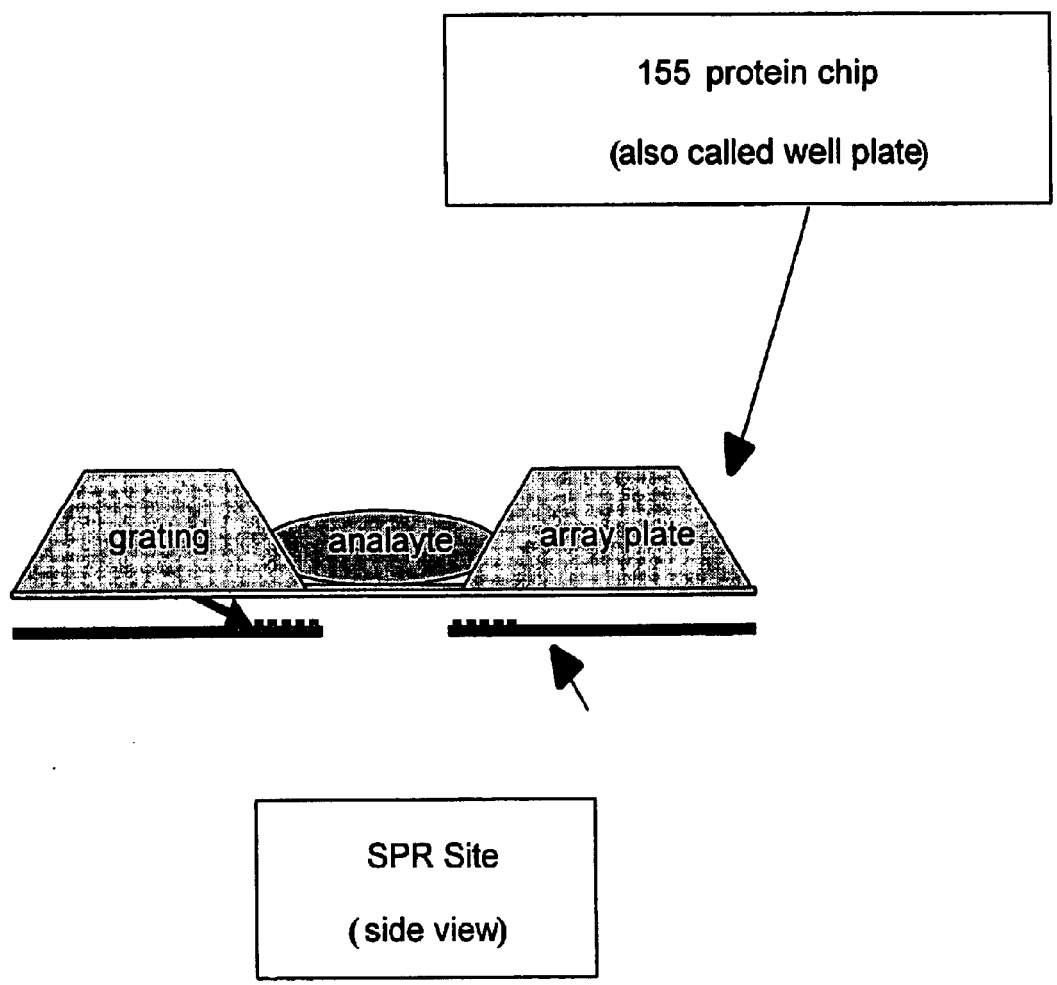
FIG. 11 illustrates cross section of a specific example of an SPR site within an SPR system in accordance with one aspect of the present invention.

Referring to FIGS. 9–11, a specific example of an SPR system 950 is shown. The SPR system 950 includes lights sources 952, an OIC 951 containing waveguide gratings 953 to couple the light to the protein chip 955 and switches 954 to route the light to specific sites on the protein chip 955.

Figure 8:
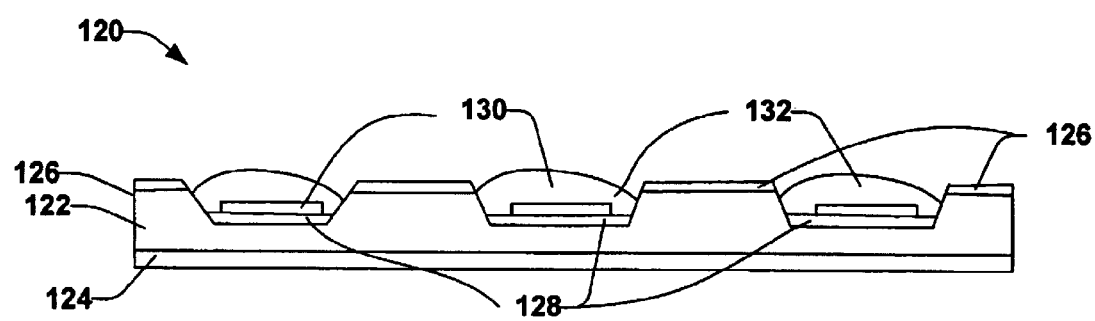
FIG. 8 illustrates a cross-sectional view of an array of microwells useful in bioanalysis systems in accordance with another aspect of the present invention.

Referring to FIG. 8, a sample array 120 is shown. The sample array 120 is made of a silicon substrate 122 with an insulation layer 124 and 126 thereover. The sample array 120 may have a disposable design. The insulation layer 124 and 126 may contain one or more of silicon dioxide, silicon nitride, silicon oxynitride, or an organic polymer (such as a polyimide). A plurality of wells is formed with the silicon substrate 122. At the bottom of the wells is a metallic layer 128 supported on an optically transparent layer typically of silicon oxide, silicon nitride, or silicon oxynitride, or a stack of two or more of these dielectric materials. The wells typically go completely through the silicon to this dielectric layer in the event that the wavelength of light being used is comparable to or significantly shorter than the energy bandgap of silicon (approximately 1150 nm); when infrared light that is appreciably longer in wavelength of the bandgap of silicon is used and certain geometries are employed, some of the silicon wafer may remain.

The metallic layer 128 contains at least one metal that is suitable for use in SPR. Examples of such metals include one or more of gold, silver, aluminum, molybdenum, and any other metal/alloy where the optical filed can be coupled to the surface plasmons. A composite 130 containing a first MBP is attached, either directly or indirectly, to the metallic layer 128. Indirect binding involves attaching a polymer, siloxane, thiol based monolayer, small molecule oligomer, or some other intermediate material to the metallic layer 128, and attaching the first MBP to the intermediate material. A second MBP, possibly having an affinity for the first MBP is contacted with the sample array 120 by depositing a solution 132 containing the second MBP into the wells.

For example, a double side polished 6 inch diameter silicon wafer of (100) orientation can be the basis for one dimensional arrays or strips of shallow microwells that integrate an optical surface and the plasmon supporting layer of metallic layer on their bottom surfaces. In one embodiment, the microwells are from about 100 to about 1,000 microns deep. In another embodiment, the microwells are from about 300 to about 500 microns deep. In yet another embodiment, the microwells are about equivalent in depth to the thickness of the silicon wafer, which is typically from about 200 to about 3,000 microns.

An insulation layer is formed on the silicon substrate. For instance, a silicon nitride layer, which may be nitride rich is formed by plasma enhanced chemical vapor deposition (PECVD) or low pressure (LP) CVD on the wafer; its thickness is adjusted according to the requirements of the coupling of the optical energy into the surface plasmon. A layer of photoresist is applied to one side of the wafer and holes are opened in the resist, the holes in one configuration having a suitable size and center to center spacing. The holes may have any suitable shape such as circular, square, rectangle, and the like. For example, center to center spacing may be from about 1 mm to about 10 mm, such as about 2.25 mm, characteristic of standard 1536 well microtiter plates. Using a plasma etch process, holes are then opened in the underlying insulation layer, exposing the silicon wafer top surface. For particular crystallographic orientations of the silicon wafer, a wet anisotropic etching process, typically utilizing KOH, creates square holes that are defined in lateral extent by the square holes in the insulation layer. The holes etch through the silicon wafer, stopping cleanly at the insulation layer on the bottom side of the wafer, and leaving a characteristically sloped sidewall with an angle of about 54.7 degrees that is a characteristic of the crystallographic planes of the silicon wafer.

The well bottoms are now composed of an insulation material, such as a SiN or SiN/SiOx of high quality. To form the metal layer required to support SPR, a metal such as gold is deposited by suitable means such as physical vapor deposition (vacuum evaporation) through a stencil type mask, onto the SiN well bottoms, with thickness optimized for the selected SPR configuration. A very thin layer of an adhesion promoting metal (such as chromium or titanium) may be optionally added. In a specific embodiment, a two dimensional array of microwell patterns on about 4 mm centers can be laid out and diced from the wafer to make 384 well microtiter plate-like with identical spacing to a typical microtiter plate. This layout is immediately compatible with commercial microdispensers, many of which are designed with a single row of pipet tips on either about 9 mm, about 4.5 mm, or about 2.25 mm spacing (for 96-, 384-, and 1536-well plates, respectively) that line up directly with the wells in the rows and columns of the disposable plate. Rows and columns may be laid out in multiple patterns, and is set to make the user interface with fluidics as straightforward as possible. By using standard silicon processing techniques, this becomes a cost effective fabrication strategy.

The microwell arrays formed in accordance with the present invention are ideally suited to SPR systems and methods, and contribute to the ability to quickly test the binding abilities of a multitude of MBPS. Since the microwell arrays formed in accordance with the present invention are easily and inexpensively fabricated, the microwell arrays are disposable. Disposability of sample arrays further improves the efficiency of SPR systems and methods. Microwell arrays containing a first MBP can be prepared well in advance of performing the SPR methods.

Additional specific examples include using a disposable analogous to a protein chip array. This is a novel high throughput platform, constructed on a metal coated planar surface, for conducting high sensitivity bioassays. Protein microarray technology is becoming an established technique for examining protein-protein interactions and other measurements. In this invention, we propose to use an SPR based protein chip concept.

An additional embodiment includes using a flat hydrophobic surface created by treating any flat substrate to create the disposable. An additional embodiment includes creating a flat substrate with additional physical barriers created to separate the regions of the chips so that isolation of the reaction may occur during testing. The disposable may additionally be produced using standards MEMS devices and techniques. Microlithography and microfabrication developed for standard MEMS semiconductor processing can be used.

The present invention effectively addresses the needs for high throughput protein identification, characterization, and screening. The present invention can distinguish between protein expression levels between normal and diseased tissue and to reconstruct protein pathways by identifying protein:protein interactions. Using protein microarrays in accordance with the present invention permits small molecule screening, toxicology profiling, and diagnostics.

Using gene chips spotted with neat rows of nanoliter sized dots of genetic materiall, and/or DNA chips, proteome chips carrying thousands of nanoliter sized dots of proteins, primed to react with any compound or set of compounds a researcher may identify is enabled. Chips can carry tens of thousands of protein capture molecules as one MBP, each geared to identify and bind to one particular protein, the other MBP. With an appropriate detection system, protein production is facilitated.

Protein microarrays used in accordance with the present invention are capable of identifying a large number of proteins in a sample and quantifying how much of each protein is present. This type of high throughput chip allows researchers to determine which proteins a gene expresses in a sample, and give doctors a tool to gather large scale protein profiles from patients.

In one embodiment, the bioanalysis systems of the present invention facilitate the accurate, rapid, and reliable detection of binding events on protein chips. Consequently, proteomics is advanced by the bioanalysis systems of the present invention owing to multiple analytical functionalities and the capability of high throughput of small volume assays. Since protein analysis is significantly more complex than conventional genomics, the present invention provides a notable advance in proteomics. The miniaturization and integration of laboratory techniques achieved by the bioanalysis systems of the present invention provides advances in existing and emerging applications, similar to the explosive transformation that occurred in the microelectronics industry throughout the last two decades. Using a chip support and/or disposable support containing multiple analytical functionalities and the capability of high throughput of small volume assays, the bioanalysis systems of the present invention are particularly well suited for biological applications that demand highly parallel, rapid, accurate, low volume assays having little or no cross contamination.

The bioanalysis systems of the present invention are useful in many specific applications. Examples of some of the areas of application include drug target discovery, validation and screening of chemical entities, combinatorial chemistry, medical diagnostics, environmental monitoring, agriculture pesticide and antibiotic monitoring, food additive testing, military and civilian airborne biological and chemical agent testing, and real time chemical and biological production process monitoring.

In particular, the use of SPR bioanalysis systems to measure binding reactions has many classes of applications. Examples of the use of SPR bioanalysis systems of the present invention include abundance measurements, equilibrium measurements, kinetic measurements, measurement of multiple analytes, and binding measurements.

An abundance measurement uses a binding reaction to estimate the concentration of an analyte in a sample. This can be achieved in various ways depending on the concentration of the analyte. For example, if the analyte is present at low abundance (less than the quantity of receptor on the surface) and has high affinity for the receptor, one can allow the binding reaction to proceed to end point (all the analyte has bound).

Equilibrium measurements can be employed when using a weakly binding analyte. In the case of a weakly binding analyte, a measurment is taken after an equilibrium condition is established. Often, end point and equilibrium measurements are very time consuming.

Kinetic measurements can be an advantageous alternative mode of setting up binding measurement. The amount of bound analyte is measured over a period of time and both the extent of binding and the time constant of the process is recorded. This method can be employed for abundance measurement since the initial rate of binding of an analyte is usually directly proportional to its concentration. Sometimes the kinetic constant of the binding reaction ("on rate") is itself of great interest. Many biological binding reactions are characterized by measurement of the "off rate"; in other words, the rate of decomposition of an existing complex. For example, in this case, a receptor is allowed to bind to its ligand, then the ligand sample in contact with the surface is quickly displaced by a solution containing no ligand. One then observes the loss of ligand from the surface as the receptor; ligand complex dissociates.

It is often desirable to measure multiple analytes of differing types. SPR methods on PLCs according to the present invention are particularly suited and advantageous for this purpose. The elimination of the need for labeling in SPR methods is even more desirable when analytes of different chemical categories are to be analyzed in parallel. This is because different chemical labeling techniques have to be adopted for each type of analyte. Moreover, the ability to locate multiple receptors within a small footprint enabled by PLC technology is advantageous in making small, economic analytic systems.

Figure 2:
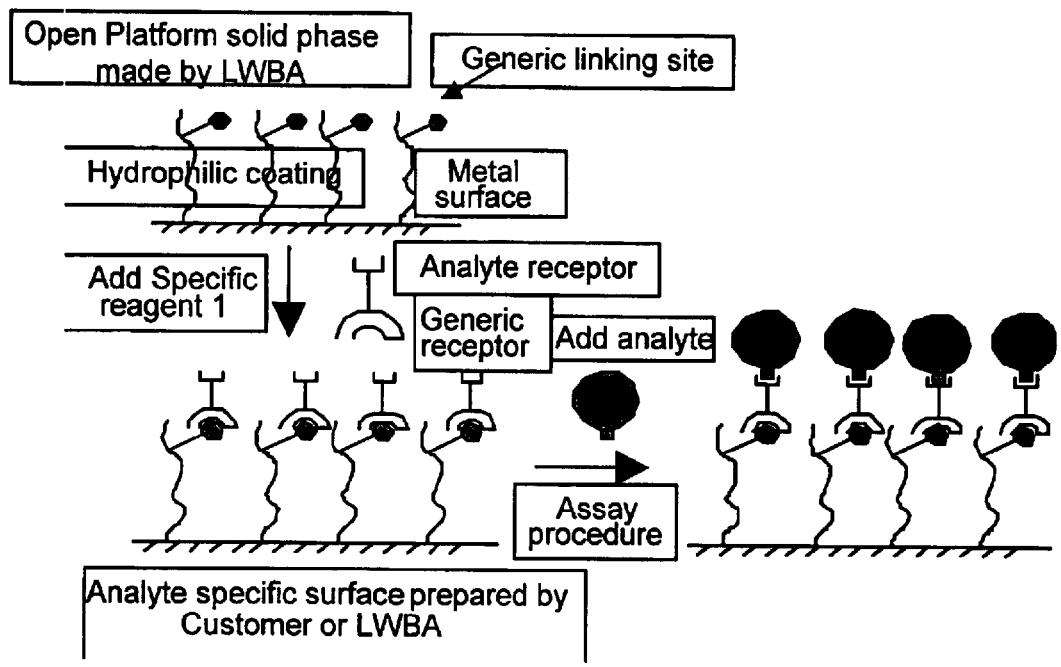
FIG. 2, illustrates a high level cross-sectional view of the chemical binding events of an SPR method in accordance with one aspect of the present invention.

Referring to FIG. 2, a high level cross sectional view of the chemical interactions/binding events of an SPR method is shown, exemplifying binding measurements. Evaluation of location and orientation of bound mass as a means to discriminate specific from nonspecific bound mass and mass not bound but adventitiously close to the metal surface (due to diffusion) is enabled by the SPR systems and methods of the present invention. Information may be derived on (a) location of bound mass (the measured parameter) in the z direction, and (b) angular orientation of mass relative to the plane of a flat SPR support. Obtaining this information is enabled by the superior resolution using PLCs.

One problem associated with conventional SPR methodology is "nonspecific binding" of mass to the SPR support surface. Such nonspecific binding compromises assay sensitivity and specificity. Nonspecific binding is, in general, located and oriented differently compared with "assay specific" binding. This is because nonspecific binding is, typically, randomly located and oriented whereas specific binding is located and oriented in a fashion determined by the specific assay chemistry. OICs enable discriminating between specific and nonspecific binding in the SPR systems and methods of the present invention, and consequently assay performance is improved.

There are many general areas of application of the SPR bioanalysis methods of the present invention. In one aspect, the SPR bioanalysis methods are broadly applicable to many areas of binding assays. Two examples include the fields of: genomics (analysis of presence, structure, interactions, and activity of genes) and proteomics (analysis of abundance, function, structure, interactions of gene products (most of which are proteins)).

In one embodiment, the SPR bioanalysis methods of the present invention facilitate the technique of "ligand fishing" used in discovery of appropriate targets for potential new drugs ("Target Discovery"). For example, often one has a receptor but does not know its function. Ligand fishing is a set of techniques in which this receptor is exposed to libraries of chemical entities or complex biological samples in the hope of finding a ligand that binds to the receptor. The nature of the ligand then provides clues to the receptor function or a tool to help elucidate its function. Often the ligand is of unknown structure. In this case, once a binding event is detected using the bioanalysis systems of the present invention, the bound ligand can be isolated from the surface and subjected to further analysis (for example by mass spectrometry) to determine or identify its structure).

Consequently, the bioanalysis systems of the present invention facilitate drug development, as the above identified functions are fundamental tools in the important process of drug development. In particular, the key areas of Target Identification, Target Validation, "ADME/Tox" (characterization of drug entity assimilation, distribution, metabolism and excretion/toxicology), library compound screening are all facilitated by the SPR bioanalysis methods and the advantages of the present invention apply directly to mitigate many of the major problems still encountered in drug development.

In another embodiment, the bioanalysis systems of the present invention facilitate clinical chemistry techniques (analysis of abundance and activity of analytes used in diagnosis of disease and monitoring of therapy). The bioanalysis systems of the present invention also facilitate analysis of environmental components such as pollutants, toxins, infectious agents and the like Industrial process control (monitoring levels of desired products or impurities in an industrial process).

There are many possible embodiments of the current invention due to the many possible configurations for the spectrometer and the specific design of the OICs used in the instrument. One specific configuration is that shown in block form in FIG. 5 and in general form in FIG. 7. In this example the SPR sample is illuminated with light of a wavelength range determined by each of the light sources 102, 103, and 104. After reflection from the SPR cell, 112, the light passes through the AWG spectrometer to a detector array. The wavelength range that reaches the individual detector in the array, 114, is now much narrower than the range from the light source. The narrow wavelength range provides an enhanced sensitivity for the measurement because the angle of the SPR signal depends on the wavelength. Multiple wavelengths of light lead to a broadening of the SPR signal and a loss of precision in the measurement. The use of the AWG made on the OIC described above enables the enhanced precision of a wavelength measurement in a small space.

In a detailed embodiment of the design shown in FIGS. 5 and 7, the elements 60 and 68 containing the optical multiplexers, optical switches and AWG are combined on a single OIC with waveguides connecting the individual components. The four individual light sources are laser diodes (LD) or light emitting diodes (LED) with broad spectral output of about 30 nm FWHM (full width half maximum) centered about 1490 nm, 1520 nm, 1550 nm, and 1580 nm. The four LDs cover the spectral range from 1475 nm to 1595 nm for the determination of the SPR angle. The LDs can be connected to the OIC by means of fiber connections from the LD to the OIC in a standard assembly process used in the optoelectronics field. (Alternatively the individual LD can be hybrid assembled onto the OIC.) The optical power from the three LD are combined into a single singlemode waveguide by means of two 2×1 splitter/combiners in a 4×1 tree configuration that is standard in integrated optics. This configuration leads to 6-dB loss due to the splitting that is 3 dB for each splitter. The advantage is that there 1×4 splitter occupies little space and is simple, since each splitter is composed of a single 2 by 2 coupler of the type described as part of the MZ switches. (Alternatively, the four wavelengths could be combined by means of a MMI (multimode interference) combiner or an AWG.)

The present invention provides high throughput protein identification, characterization, and screening. In part, the systems and methods of the present invention discriminate between protein expression levels between normal and diseased tissue and to reconstruct protein pathways by identifying protein:protein interactions. Protein microarrays are particularly useful for small molecule screening, toxicology profiling, and diagnostics.

This present invention provides a chip/disposable containing multiple analytical functionalities and the capability of high throughput of small volume assays. These systems and methods of the present invention are particularly well suited for biological applications that demand highly parallel, rapid, accurate, low volume assays having little or no cross contamination.

The following examples illustrate the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

Preparation of Receptor Coated Gold Surface

Gold surfaces are prepared and washed using (1) water, (2) ethanol. The gold surfaces are then exposed to at least 5 $\mu$L/mm$^2$ of 10 mM 11-mercaptoundecanoic acid (MUA) dissolved in ethanol overnight at RT. The surfaces are then washed using (1) ethanol, (2) 50% ethanol/water, (3) 25% ethanol/water, (4) water then dried. The MUA treated gold surface is then exposed to at least 5 $\mu$L/mm$^2$ of 100 mM N-ethyl-N1-(dimethylaminopropyl)carbodiimide (EDCI) and 40 mM N-Hydroxysuccinimide (NHS) in 50 mM MES-Na, at pH 5.0 at RT for 30 min to form an NHS-ester of the MUA. The NHS-ester surfaces are washed with PBS (Phosphate buffered saline) then exposed to streptavidin (10 $\mu$g/mL) in PBS for 30 min at RT. Finally the gold surface linked to streptavidin is washed with PBS.

EXAMPLE 2

Incorporation of a Receptor into a Microwell Array

The gold surfaces of the microwell array are coupled to streptavidin according to the procedure of Example 1.

EXAMPLE 3

Incorporation of a Receptor into a 2 Dimensional Array

Streptavidin is coupled to the gold surface of a 2 dimensional array constructed using the method of Example 1. A set of biotinylated receptors (prepared by literature methods) is bound to the streptavidin coated surface by "printing" small volumes of receptor solutions (0.5 µL of each at 10 µg/mL in PBS) at known locations on the surface spaced apart by more than 2 mm. After a brief incubation (2 min), unbound receptors are removed by washing the array with PBS.

EXAMPLE 4

Assay Protocol Using Microwell Array

Microwell arrays are coated with streptavidin according to Example 1 and 5 µL of PBS is placed in each well. Samples are tested for the presence of biotinylated proteins by preparing aqueous solutions of test samples in PBS and applying equal 5 µL aliquots to each well after aspiration of the PBS buffer. Serial SPR measurements are made over a five minute time period and measurements made after 30 sec and each subsequent one minute period are compared.

EXAMPLE 5

Assay Protocol Using a 2 Dimensional Array

2-Dimensional arrays are made and coated with several different protein kinases according to Example 1. Test samples dissolved in PBS were evaluated for binding to these kinases by flooding the arrays with 5 µL/mm$^2$ of the test solution. Serial SPR measurements are made over a five minute time period and measurements made after 30 sec and each subsequent one minute period are compared.

EXAMPLE 6

Receptor Containing Lipid Bilayer Interface

Development of a robust biosensor requires the successful capture of functional proteins in a matrix that is able to interact with a receptor. Research has demonstrated the ability to capture single functional enzymes in polymer matrices. (Gill, I.; Ballesteros, A.; "Bioencapsulation within synthetic polymers (Part 2): non-sol gel protein polymer biocomposites", Trends in Biotechnology, 18,469–479, 2000. LeJeune, K. E.; Russell, A. J.; "Covalent Binding of a Nerve Agent Hydrolyzing Enzyme within polyurethane foams", Biotechnology and Bioengineering; 51, 450–457, 1996.), which are hereby incorporated by reference for their relevant teachings in this regard. However, to date, immobilization of protein signaling cascades resulting in signal amplification has not been demonstrated. G-protein systems are an important family of proteins that are currently being studied extensively due to their role in health and disease. The purified receptors are reconstituted in functional form into a lipid bilayer membrane that can be attached at the gold surface of the detector. For example, the reconstitution of the bacterial expressed GPCR into phosphatidylcholine:phosphatidylglycerol (4:1) liposomes is possible. A GPCR can be incorporated into a cell membrane hybrid bilayer formed from COS-1 cell membranes at a gold surface for the purpose of performing surface plasmon resonance analysis. The COS-1 cell membranes with the overexpressed receptors contained 0.08% of the total membrane protein as the receptor.

In order to increase the relative amount of receptor in our membrane, a purification procedure can be performed and the pure receptors can be reconstituted into liposome vesicles that mimic the cell membranes and fused to planar membranes. In some instances it can be important to start with purified membrane protein in order to obtain the maximum possible signal output of the instrument. Another approach involves an amine coupling of detergent-solubilized rhodopsin, also a 7 transmembrane receptor protein, to the gold layer followed by a titration of the detergent away by flowing liposomes over the surface. The resulting surface contains about 4 ng.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A surface plasmon resonance system, comprising:
    a support comprising a metal film, a first medium adjacent a first side of the metal film and a second medium adjacent a second side of the metal film;
    an illumination source operable to illuminate at least one incident region of the metal film through the first medium;
    at least one assay region on the second side of the metal film opposing the incident region; and
    a collector operable to collect illumination reflected from the metal film;
    wherein at least one of the illumination source and the collector comprise an optical integrated circuit, the optical integrated circuit comprises at least one arrayed waveguide grating spectrometer.

2. The surface plasmon resonance system according to claim 1, wherein the arrayed waveguide grating spectrometer comprises more than about 500 channels.

3. The surface plasmon resonance system according to claim 1, wherein the second medium comprises a first member of a binding pair and a second member of a binding pair.

4. The surface plasmon resonance system according to claim 3, wherein the first member of a binding pair and the second member of a binding pair are independently selected from the group consisting of antigen, antibody, hormone, hormone receptor, polynucleotide, avidin, streptavidin, biotin, enzyme, enzyme substrate or inhibitor, lectins, specific carboxyhydrate, lipids, lipid binding proteins or membrane associated proteins, polynucleotides, polynucleotide binding proteins, receptor, transmitter, drug, target, protein, small molecule having a molecular weight of about 2,000 or less, polynucleic acid, DNA, and RNA.

5. The surface plasmon resonance system according to claim 3, wherein at least one of the first member of a binding pair and the second member of a binding pair have a molecular weight of about 2,000 or less.

6. The surface plasmon resonance system according to claim 1, wherein the metal film comprises at least about 100 incident regions and at least about 100 corresponding assay regions, the illumination source operable to illuminate the at least about 100 incident regions.

7. The surface plasmon resonance system according to claim 1, wherein the metal film is comprised within one of a gene chip, a DNA chip, or a protein chip.

8. The surface plasmon resonance system according to claim 1, wherein the second medium comprises a first member of a binding pair immobilized to the metal film in the assay region.

9. The surface plasmon resonance system according to claim 1, wherein the metal film comprises at least one of gold, silver, aluminum, and molybdenum, and the first medium comprises at least one of a plastic, borosilicate glass, phosphosilicate glass, and silica glass.

10. The surface plasmon resonance system according to claim 1, wherein the optical integrated circuit further comprises an integrated optical switch.

11. A method of monitoring a binding event, comprising:
  illuminating a metal film through a first medium adjacent one side of the metal film, an assay medium comprising a first member of a binding pair immobilized on a second side of the metal film;
  contacting the first member of a binding pair with a second member of a binding pair;
  collecting illumination reflected from the metal film; and
  analyzing properties of the collected illumination;
  wherein at least one of illuminating the metal film and collecting illumination comprises using an optical integrated circuit, the optical integrated circuit comprises at least one arrayed waveguide grating spectrometer.

12. The method according to claim 11, wherein illuminating the metal film comprises using light having a wavelength from about 390 nm to about 2,500 nm.

13. The method according to claim 11, wherein at least about 225 assay media each comprising a first member of a binding pair are immobilized on the second side of the metal film.

14. The method according to claim 13, wherein the assay media each have a volume of about 0.5 µL or less.

15. The method according to claim 11, wherein analyzing properties of the reflected light determines at least one of a) measuring an amount of the second member of a binding pair bound to the first member of a binding pair in the assay, b) whether or not binding occurs between the first member of a binding pair and the second member of a binding pair, and c) distinguishing between specific and non-specific binding between the first member of a binding pair and the second member of a binding pair.

16. The method according to claim 11, wherein the optical integrated circuit uses a 2×N optical switch to directing light at the metal film.

17. The method according to claim 11, wherein at least one of the first member of a binding pair and the second member of a binding pair have a molecular weight of about 2,000 or less.

18. The method according to claim 11, wherein the first member of a binding pair and the second member of a binding pair are independently selected from the group consisting of antigen, antibody, hormone, hormone receptor, polynucleotide, avidin, streptavidin, biotin, enzyme, enzyme substrate or inhibitor, lectins, specific carboxyhydrate, lipids, lipid binding proteins or membrane associated proteins, polynucleotides, polynucleotide binding proteins, receptor, transmitter, drug, target, protein, small molecule having a molecular weight of about 2,000 or less, polynucleic acid, DNA, and RNA.

19. The method according to claim 11, wherein the optical integrated circuit further comprises an integrated optical switch.

20. A microwell array for a surface plasmon resonance system, comprising:
  a silicon substrate comprising a plurality of wells to accommodate an interaction between a first member of a binding pair and a second member of a binding pair;
  a metal layer coupled to the silicon substrate so as to be positioned at the bottom of the wells;
  an insulation layer adjacent the metal layer;
  an optical integrated circuit connected to the insulation layer, the optical integrated circuit comprising an arrayed waveguide grating spectrometer, the optical integrated circuit configured to illuminate each of the plurality of wells.

21. The microwell array according to claim 20, wherein the silicon substrate comprises at least about 400 wells.

22. The microwell array according to claim 20, wherein the plurality of wells independently comprise at least one selected from the group consisting of antigen, antibody, hormone, hormone receptor, polynucleotide, avidin, streptavidin, biotin, enzyme, enzyme substrate or inhibitor, lectins, specific carboxyhydrate, lipids, lipid binding proteins or membrane associated proteins, polynucleotides, polynucleotide binding proteins, receptor, transmitter, drug, target, protein, small molecule having a molecular weight of about 2,000 or less, polynucleic acid, DNA, and RNA.

23. The microwell array according to claim 20, wherein the metal film comprises at least one of gold, silver, aluminum, and molybdenum, and the first medium comprises at least one of a plastic, borosilicate glass, phosphosilicate glass, and silica glass.

* * * * *